United States Patent
Shirizly et al.

(10) Patent No.: US 11,918,418 B1
(45) Date of Patent: Mar. 5, 2024

(54) ULTRASOUND IMAGING SYSTEMS, DEVICES AND METHODS THAT SIMULATE A VIRTUAL MOVING TRANSDUCER/RECEIVER TO IMPLEMENT A SYNTHETIC APERTURE ARRAY

(71) Applicant: ORCASONICS INNOVATION LTD., Ra'anana (IL)

(72) Inventors: Matityahu Shirizly, Modi'in-Maccabim-Re'ut (IL); Alexander Lomes, Moshav Hosen (IL)

(73) Assignee: ORCASONICS INNOVATION LTD, Ra'anana (IL)

( * ) Notice: Subject to any disclaimer, the term of this patent is extended or adjusted under 35 U.S.C. 154(b) by 0 days.

(21) Appl. No.: 18/214,570

(22) Filed: Jun. 27, 2023

Related U.S. Application Data

(60) Provisional application No. 63/457,526, filed on Apr. 6, 2023.

(51) Int. Cl.
*A61B 8/08* (2006.01)

(52) U.S. Cl.
CPC ............ *A61B 8/488* (2013.01); *A61B 8/5207* (2013.01); *A61B 8/5223* (2013.01)

(58) Field of Classification Search
None
See application file for complete search history.

(56) References Cited

U.S. PATENT DOCUMENTS

| | | | | |
|---|---|---|---|---|
| 5,083,568 | A * | 1/1992 | Shimazaki | G10K 11/345 600/459 |
| 5,243,988 | A * | 9/1993 | Sieben | A61B 8/445 600/463 |

(Continued)

FOREIGN PATENT DOCUMENTS

WO    WO 2012/160541    11/2012

OTHER PUBLICATIONS

Jensen et al. 2010, "Implementation of synthetic aperture imaging in medical ultrasound: the dual stage beamformer approach", European Conference on Synthetic Aperture Radar IEEE.

Zhuang et al. 2022, "Frequency-Domain Beamforming Without Interpolation Using the Chirp Scaling Algorithm", IEEE IUS—International Ultrasound Symposium 2022, lecture abstract.

(Continued)

*Primary Examiner* — John D Li
(74) *Attorney, Agent, or Firm* — PEARL COHEN ZEDEK LATZER BARATZ LLP

(57) ABSTRACT

Ultrasound imaging systems, devices, patches and methods are provided, which implement a linear transducer-receiver array to simulate a virtual moving transmitter-receiver, implementing a virtual synthetic array for ultrasound, to generate far field ultrasound images from Range-Doppler maps of body regions, beyond surface obstructions (such as ribs). The Range-Doppler maps are derived using an ultra-wideband frequency modulated (UWFM) ultrasound signal, adjusting the transmission and reception parameters to optimize the derived signals. The signals are compressed laterally, independently for each range-gate, forming a long and narrow beam and a convolution window that is growing with the range—achieving uniformly high resolution. The transducer array is configured to have a designed autofocusing beam, and multiple images with different phase relations between the receivers are combined to create trapezoidal-like ultrasound image. The operation characteristics yield very low power dissipation that allows for long term monitoring of patients.

14 Claims, 16 Drawing Sheets
(2 of 16 Drawing Sheet(s) Filed in Color)

(56) References Cited

U.S. PATENT DOCUMENTS

| | | | | |
|---|---|---|---|---|
| 5,735,281 | A * | 4/1998 | Rafter | A61B 5/352 600/458 |
| 11,129,586 | B1 * | 9/2021 | Moore | A61B 8/02 |
| 2006/0100516 | A1 * | 5/2006 | Hossack | G01S 7/52088 600/447 |
| 2006/0241425 | A1 * | 10/2006 | Payne | A61B 8/02 600/437 |
| 2013/0079621 | A1 * | 3/2013 | Shoham | A61M 37/0092 600/407 |
| 2014/0088429 | A1 * | 3/2014 | Lomes | A61B 8/145 600/443 |
| 2015/0011883 | A1 * | 1/2015 | Belt | A61B 8/461 600/443 |
| 2015/0133787 | A1 * | 5/2015 | Wegner | G01S 15/8952 600/447 |
| 2015/0164473 | A1 * | 6/2015 | Kim | A61B 8/4494 600/443 |
| 2016/0022308 | A1 * | 1/2016 | Rohling | A61M 5/46 604/117 |
| 2018/0085096 | A1 * | 3/2018 | Brandl | A61B 8/469 |

OTHER PUBLICATIONS

Buffi, A. et al; Design Criteria for Near-Field-Focused Planar Arrays; Authorized licensed use limited to: Ben-Gurion University of the Negev. Downloaded on Oct. 18, 2023 at 11:35:42 UTC from IEEE Xplore.

Maxim Integrated Products; Tutorial 1890; An Introduction to Spread-Spectrum Communications; Feb. 18, 2003.

Xu Zongze et al; Large time-bandwidth product processing of signals in spread-spectrum communications; National Air Intelligence Center; Jan. 7, 1997; Translation of "Kuo Pin Tong Xin Zhong Xin Hao De Da Shi Dai Ji Chu Li"; Journal of China Institute of Communications, vol. 13, No. I. Jan. 1992, pp. 8-16.

Farnett Edward C. et al; Pulse Compression Radar; Chapter 10; RCA Electronic Systems Department GE Aerospace; Radar Handbook, edited by Merrill I. Skolnik; second edition; 1990.

Sophocles J. Orfanidis; Radiation Fields; Electromagnetic Waves and Antennas, 2016.

Balanis, Constantine A.; Antenna Theory Analysis and Design; John Wiley & Sons Inc; 2005.

\* cited by examiner

ULTRASOUND IMAGING SYSTEMS, DEVICES AND METHODS THAT SIMULATE A VIRTUAL MOVING TRANSDUCER/RECEIVER TO IMPLEMENT A SYNTHETIC APERTURE ARRAY

CROSS REFERENCE TO RELATED APPLICATIONS

This application claims priority from U.S. Provisional Application No. 63/457,526, filed on Apr. 6, 2023, which is incorporated herein by reference in its entirety.

BACKGROUND OF THE INVENTION

1. Technical Field

The present invention relates to the field of ultrasound imaging, and more particularly, to ultrasound imaging that simulates a virtual moving transmitter-receiver to implement virtual synthetic array ultrasound.

2. Discussion of Related Art

Jensen et al. 2010 (Implementation of synthetic aperture imaging in medical ultrasound: the dual stage beamformer approach, European Conference on Synthetic Aperture Radar IEEE), which is incorporated herein by reference in its entirety, teaches a method for reducing the number of calculations needed for real time synthetic aperture (SA) imaging, while retaining the capability of SA imaging to visualize dynamic structures in the human body—by implementing a dual stage beamformer including a simple fixed focus analog beamformer and an ordinary digital ultrasound beamformer.

WIPO Publication No. 2012160541, which is incorporated herein by reference in its entirety, teaches a method of producing an ultrasound image of an imaging region of a body, the image comprising pixels, the method comprising: a) transmitting time-varying ultrasound into the imaging region, over a time interval, from a surface of the body, the transmitted ultrasound simultaneously having an angular spread in the imaging region corresponding to a plurality of the pixels of the image; and b) receiving echoes of the transmitted ultrasound, and recording received signals of the echoes; wherein one or both of the transmitting and the receiving is done at a different location during each of a plurality of different sub-intervals of the time interval; and c) combining the received signals at the different sub-intervals of the time interval based on said time varying, according to expected ultrasound propagation times to scatterers localized at different pixels, to find image densities at the pixels.

Zhuang et al. 2022 (Frequency-Domain Beamforming Without Interpolation Using the Chirp Scaling Algorithm, IEEE IUS—International Ultrasound Symposium 2022, lecture abstract), which is incorporated herein by reference in its entirety, teaches the adaptation of the chirp scaling algorithm (CSA) to ultrasound imaging with multistatic synthetic aperture data, teaching away from time-domain and frequency-domain beamforming methods such as delay and sum (DAS) and range-Doppler algorithm (RDA), respectively.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides an ultrasound imaging system comprising: a source configured to generate an ultra-wideband frequency modulated (UWFM) ultrasound signal, an array of micromachined ultrasound transducers, configured to be coupled to a patient body, a controller configured to transmit the generated ultrasound signal and to receive an ultrasound signal from the patient body—sequentially through the transducers to the body by switching the transducers according to a predefined pattern, and an image processing unit configured to analyze the received ultrasound signals with respect to the transmitted ultrasound signals and the predefined transmission pattern and generate a far field ultrasound image of a region of interest (ROI) in the patient body, wherein: the predefined pattern simulates a moving transmitter and a moving receiver having a virtual velocity, and the image processing unit is configured to generate the ultrasound image as a Range-Doppler map of the ROI.

One aspect of the present invention provides a method of ultrasound imaging, the method comprising: generating ultra-wideband frequency modulated (UWFM) ultrasound signals, transmitting the generated ultrasound signals and receiving ultrasound signals via an array of micromachined ultrasound transducers that are coupled to a patient body, wherein the transmitting and receiving are carried out sequentially through the transducers to the body by switching the transducers according to a predefined pattern that simulates a moving transmitter and a moving receiver having a virtual velocity, analyzing the received ultrasound signals with respect to the transmitted ultrasound signals and the predefined transmission pattern, and generating a far field ultrasound image of a region of interest (ROI) in the patient body, as a Range-Doppler map of the ROI.

One aspect of the present invention provides a computer program product comprising a non-transitory computer readable storage medium having computer readable program embodied therewith, the computer readable program comprising: computer readable program configured to generate ultra-wideband frequency modulated (UWFM) ultrasound signals, computer readable program configured to transmit the generated ultrasound signals and receiving ultrasound signals via an array of micromachined ultrasound transducers that are coupled to a patient body, wherein the transmitting and receiving are carried out sequentially through the transducers to the body by switching the transducers according to a predefined pattern that simulates a moving transmitter and a moving receiver having a virtual velocity, computer readable program configured to analyze the received ultrasound signals with respect to the transmitted ultrasound signals and the predefined transmission pattern, and computer readable program configured to generate a far field ultrasound image of a region of interest (ROI) in the patient body, as a Range-Doppler map of the ROI.

These, additional, and/or other aspects and/or advantages of the present invention are set forth in the detailed description which follows, possibly inferable from the detailed description, and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout. The patent or application file contains at least one drawing executed in color. Copies of this patent or patent application publication with color drawing(s) will be provided by the Office upon request and payment of the necessary fee. In the accompanying drawings.

Figure 1:
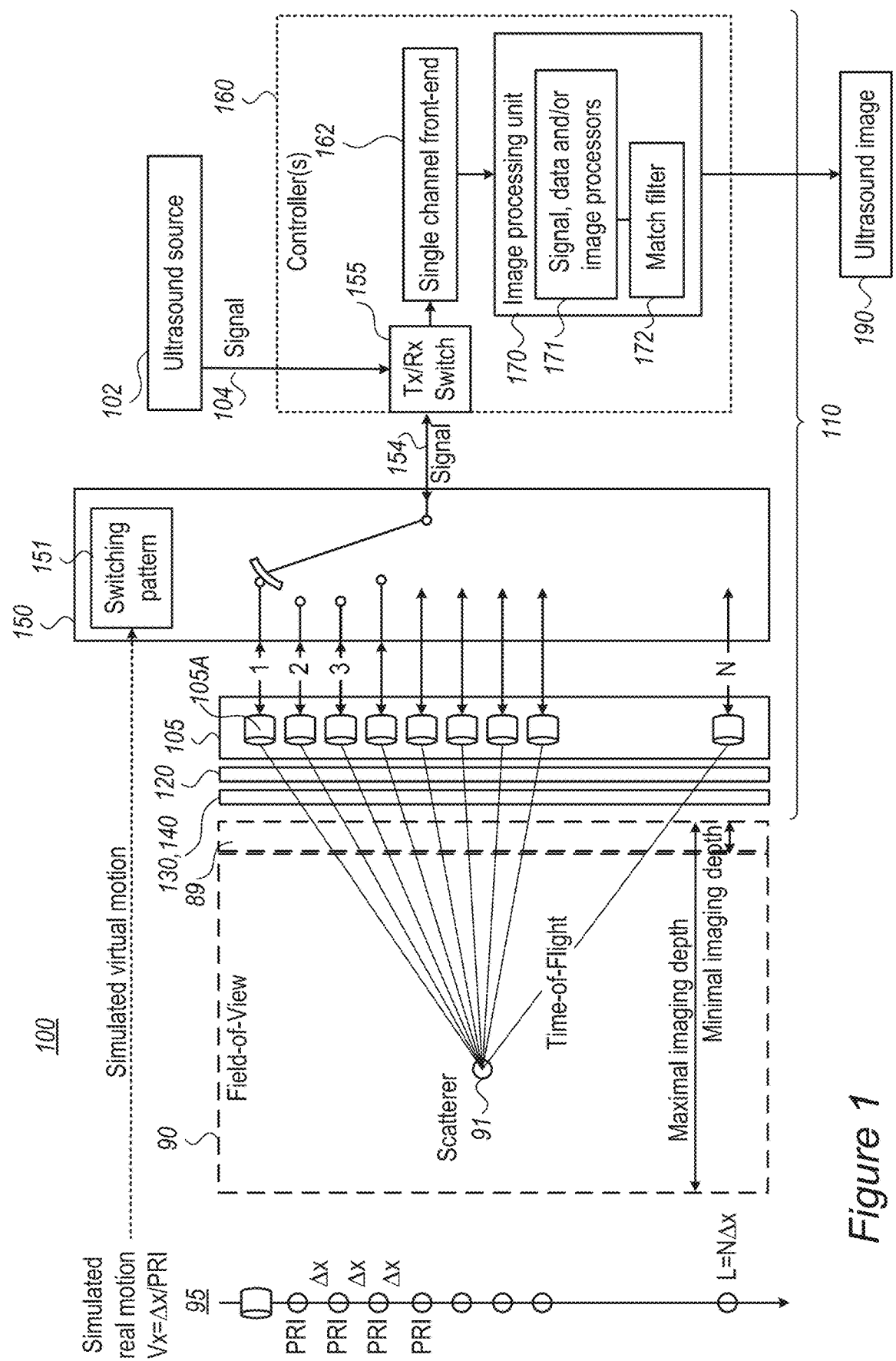
FIG. 1 is a high-level schematic block diagram of an ultrasound imaging system, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well-known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Unless specifically stated otherwise, as apparent from the following discussions, it is appreciated that throughout the specification discussions utilizing terms such as "processing". "computing". "calculating", "determining". "enhancing". "deriving" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Some embodiments of the present invention provide efficient and economical methods and mechanisms for enabling low power ultrasound monitoring and thereby provide improvements to the technological field of ultrasound imaging. Ultrasound imaging systems, devices, patches and methods are disclosed, which implement a linear transducer-receiver array to simulate a virtual moving transmitter-receiver, implementing virtual synthetic array for ultrasound, to generate far field ultrasound images from Range-Doppler maps of body regions, beyond surface obstructions (such as ribs). The Range-Doppler maps are derived using an ultra-wideband frequency modulated (UWFM) ultrasound signal, adjusting the transmission and reception parameters to optimize the derived signals. The signals are compressed laterally, independently for each range-gate, forming a long and narrow beam and a convolution window that is growing with the range—achieving uniformly high resolution, processing images using long chirps as UWFM signal. The transducer array is configured to have a designed autofocusing beam, and multiple images with different phase relations between the receivers are combined to create trapezoidal-like ultrasound image. Moreover, the operation characteristics yield very low power dissipation that allows for long term monitoring of patients.

In the following, ultrasound imaging systems and methods are provided, as well as low power patches and corresponding hydro-gel designs.

Figure 2A:
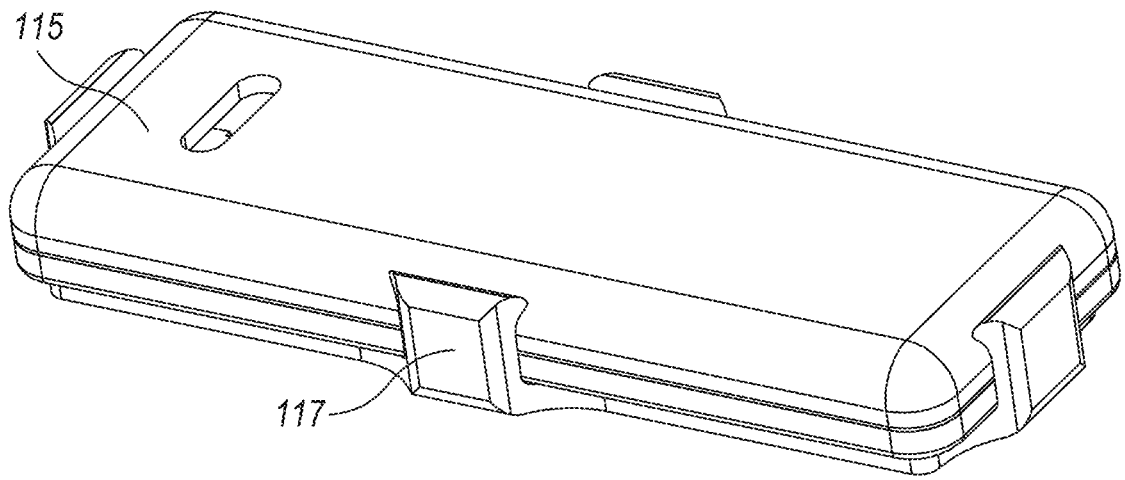
FIGS. 2A-2E are high-level schematic illustrations of low power patches that are operable within ultrasound imaging system. e.g., as at least partly disposable units, according to some embodiments of the invention.
Figure 2B:
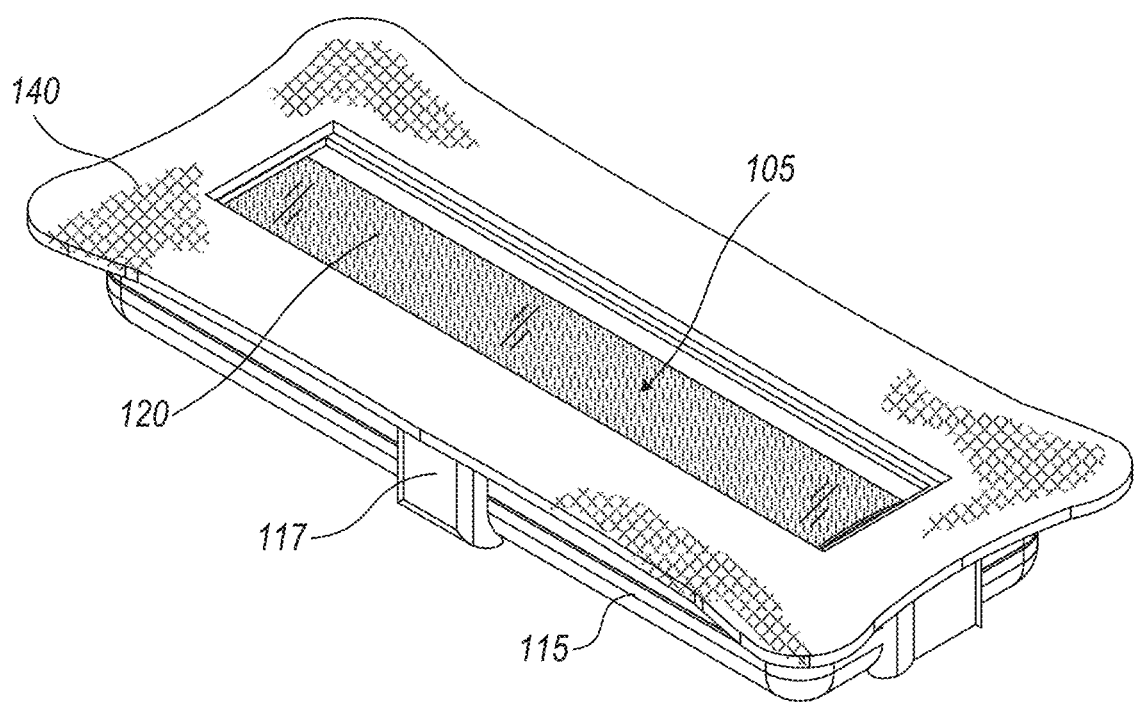
Figure 2C:
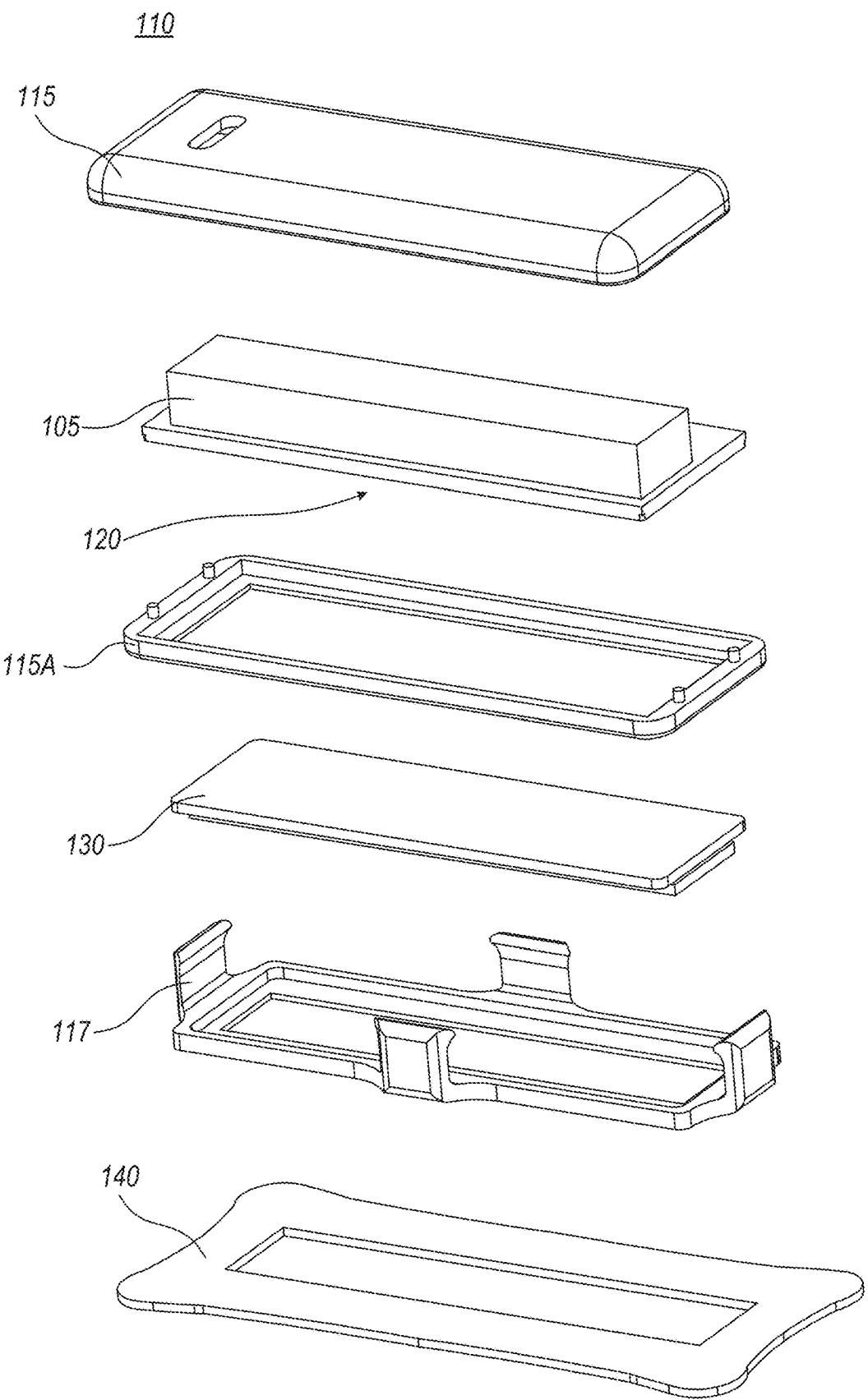
Figure 2E:
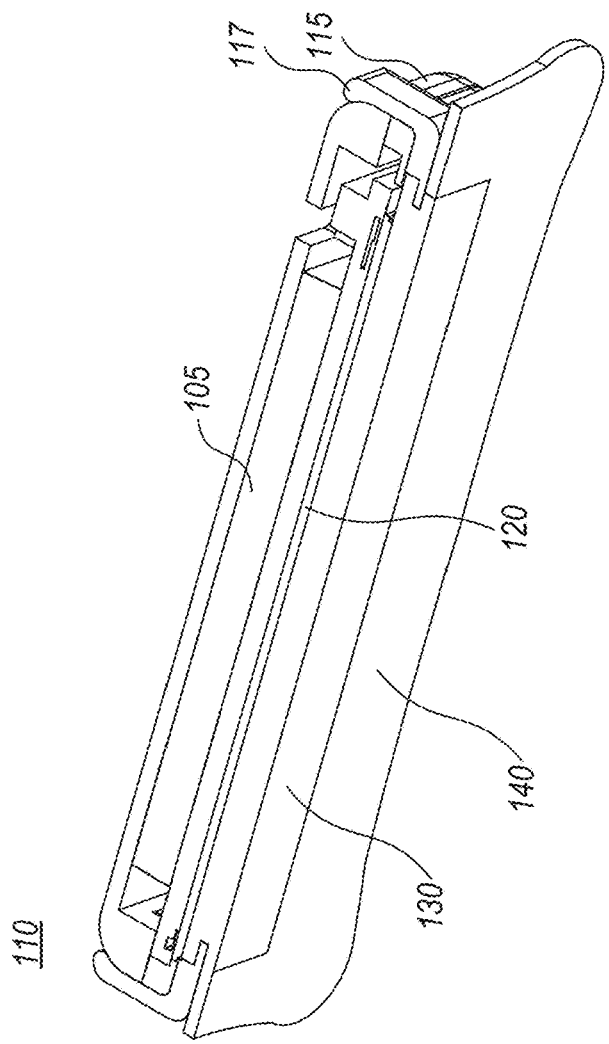
Figure 2D:
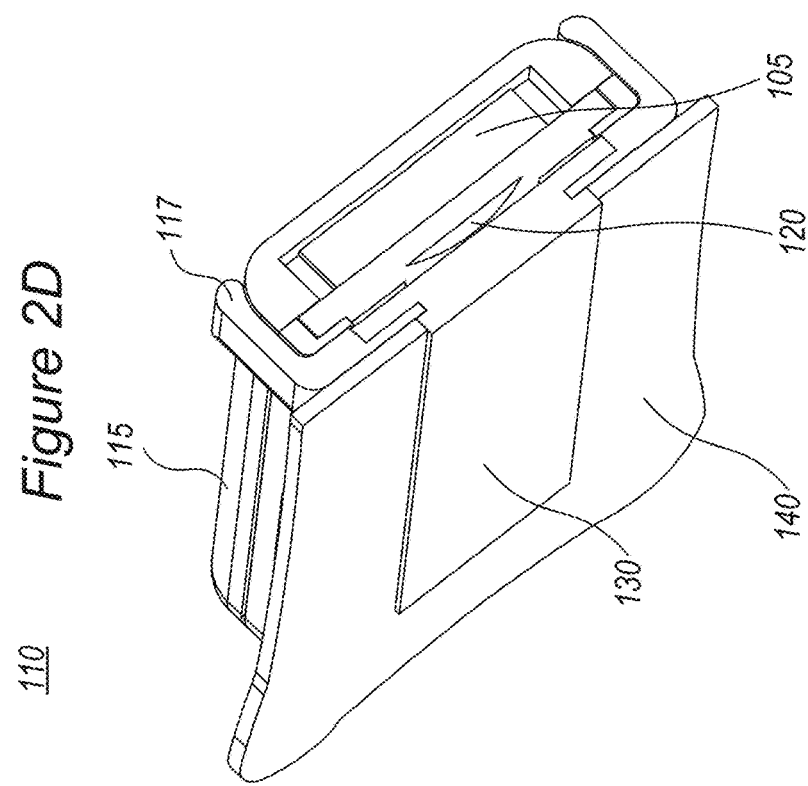

FIG. 1 is a high-level schematic block diagram of an ultrasound imaging system 100, according to some embodiments of the invention. FIG. 1 provides a highly and non-limiting schematic illustration of systems 100 and their operation principles, according to some embodiments of the invention. FIGS. 2A-2E are high-level schematic illustrations of low power patch 110 that are operable within ultrasound imaging system 100, e.g., as at least partly disposable units, according to some embodiments of the invention. FIGS. 2A and 2B provide backside and front perspective views of low power patch 110, respectively, according to some embodiments of the invention. FIG. 2C provides a perspective exploded view of low power patch 110, according to some embodiments of the invention. FIGS. 2D-2E provide additional schematic traverse and longitudinal cross section views, according to some embodiments of the invention. FIGS. 3A-3D are images of an experimental prototype of low power patch 110 and a possible design of a hydro-gel coupling 130, according to some embodiments of the invention. FIGS. 4A and 4B are high-level schematic top and perspective illustrations of an ultrasound lens 120 of low power patch 110, respectively, according to some embodiments of the invention.

Disclosed ultrasound imaging system comprise, in some embodiments, a source 102 (e.g., a single-channel ultrawideband nonlinear frequency modulated (NLFM) 3-level pulser) configured to generate an ultra-wideband frequency modulated (UWFM) ultrasound signal 104, an array 105 of micromachined ultrasound transducers 105A, configured to be coupled to a patient body, a controller 160 configured to transmit the generated ultrasound signal (104) and to receive an ultrasound signal 154 from the patient body—sequentially through transducers 105A to the body by switching transducers 105A according to a predefined pattern 151, and an image processing unit 170 configured to analyze the received ultrasound signals (154) with respect to the transmitted ultrasound signals (104) and the predefined transmission pattern (151) and generate an ultrasound image 190 of a region of interest (ROI) in the patient body. Array 105 may include any number of transducers 105A. e.g., 5, 10, 20, 40, or any intermediate or larger number of transducers 105A, with associated electronics.

As illustrated schematically in FIG. 1, in some embodiments the predefined pattern (151) may be configured to simulate a moving transmitter and a moving receiver (denoted 95 as a conceptual model) having a virtual velocity (Vx=Δx/PRI, with Δx the distance between simulated transducers and PRI—pulse repetition interval), and image processing unit 170 may be configured to generate a far field ultrasound image 190 as a Range-Doppler map of the ROI. It is noted that in FIG. 1, a field of view (FOV) 90 with scatterers 91 (one is illustrated in a non-limiting manner to provide a representation of the respective parameter of time of flight with respect to the simulated movement) is shown schematically, and would typically comprise at least part of the ROI in the patient body. FOV 90 is defined between a minimal and a maximal imaging depth, further discussed below. Possibly an obstructing region 89, such as obstruction body parts (e.g., ribs) may be included within the minimal imaging depth, and disclosed imaging systems and methods may be configured to overcome the obstruction presented by region 89 to image FOV 90 without obstruction, shadowing, etc., as explained below. Disclosed embodiments reduce or eliminate shadowing by obstructing structures (e.g., bones, air gaps, bubbles, etc.) and provide image reconstructions of ultrasound scatterers 91 located, e.g., behind the ribs of the human chest.

In various embodiments, micromachined ultrasound transducers 105A may comprise. e.g., capacitive micromachined ultrasound transducers, CMUTs. and/or piezoelectric micromachined ultrasonic transducer, PMUTs, or optionally regular piezoelectric transducers or ultrasound transducers of other types. In some embodiments, array 105 of micromachined ultrasound transducers 105A may be linear (1D), and the predefined switching pattern (151) may include switching one transducer 105A as the transmitter/receiver (Tx/Rx) at a time. In some embodiments, array 105 of micromachined ultrasound transducers 105A may be two-dimensional (2D), and the predefined pattern (151) may include switching at least two transducers 105A at a time to yield a virtual (simulated) Tx/Rx movement implemented by the predefined pattern (151) in the lateral direction, while the imaging in the elevation direction may be provided by a linear array combined or not with an acoustical lens.

In various embodiments, at least some of the components of systems 100 may be integrated within a low power patch device 110, which may be partly or fully disposable. For example, ultrasound low power patch 110 may comprise CMUT transducer array 105, controller elements such as a switching unit 150 (e.g., an N-by-1 analog switch implementing switching pattern 151) associated with a Tx/Rx switch 155 and a single channel front-end 162 (including, e.g., a single-channel receiver and/or a digital down-converter (DDC) complex frame matrix), and image processing unit elements such as signal/data processor(s) and/or image processor(s) 171, possibly associated with or including a match filter 172 as disclosed herein. Examples for patch design and implementations are provided, as non-limiting examples, in FIGS. 2A-2E. Ultrasound imaging system 100 may be further configured to provide feedback and/or instructions to enable optimal positioning of patch 110 on the patient (e.g., on the patient's chest, above the heart) in particular to conform with the body region contours of the specific patient and positioning location.

As illustrated schematically in the non-limiting device embodiments illustrated schematically in FIGS. 2A-2E and 3A-3D, a part with transducer array 105 (beneath ultrasound lens 120) and processors parts of the device may be clamped onto the tissue interface part 140 of device 110 for various implementations (e.g., partial disposability, better fitting), and interface part 140 together with hydro-gel coupling 130 may be configured to match the tissue index and to enable full attachment to the body's curved surface leaving no air gap in between. Interface part 140 may include and/or be attached to hydrogel element 130 described herein. Ultrasound lens 120 may be part of and/or attached to device 110 to provide good beam forming and/or focusing properties, as explained herein (see, e.g., FIGS. 4A and 4B illustrating schematically a non-limiting design). Lens 120 may be clamped between parts of device 110 and/or be integrated with parts of transducer array 110 and/or with tissue interface part 140. In certain embodiments, the focusing and index matching component(s) 120, 130 may be spatially separate and not interfere with tissue attachment and fixation part 140. For example, focusing and index matching component(s) 120, 130 may be set at a central position while tissue attachment and fixation part 140 may be set at a circumferential position, with or without at least partial overlap. Disclosed embodiments provide easy and optimal positioning of patch device 110 on the patient's conformal body, e.g., via the configuration of tissue interface part 140 and/or hydrogel element 130.

Patch device 110 may further comprise fixating elements (e.g., tape, suction, adhesion, etc., which may be part of tissue interface part 140 and/or be attached thereto) configured to fixate patch device 110 to the body at the correct position, provide the required field of view (FOV) 90, possibly enabling slight adjustments if required without moving patch device 110. Embodiments of patch device 110 may comprise a snap-in frame and connector(s) 115, 117, respectively, configured to hold transducer array 105. Embodiments of patch device 110 may comprise a molded index matching cushion 120 as at least part of ultrasound lens 120 at the center that does not leave residues on the tissue and does not interfere with adhesion (see, e.g., FIGS. 2B and 3A). Embodiments of patch device 110 may comprise sticky edges as a non-limiting embodiment of tissue attachment and fixation part 140 on frame 115, which provide the adhesion to the body see, e.g., FIGS. 2B and 3A-3C). Embodiments of patch device 110 may comprise built-in and/or detachable PMUT/CMUT ultrasound sensor array(s) 105 (see, e.g., FIGS. 2A-2E and 3A).

Figure 3D:
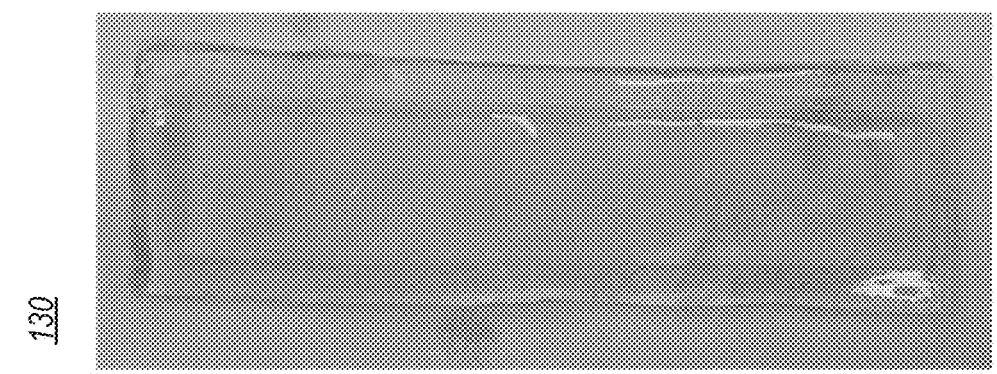
FIGS. 3A-3D are images of an experimental prototype of a low power patch and a possible design of a hydro-gel coupling, according to some embodiments of the invention.
Figure 3C:
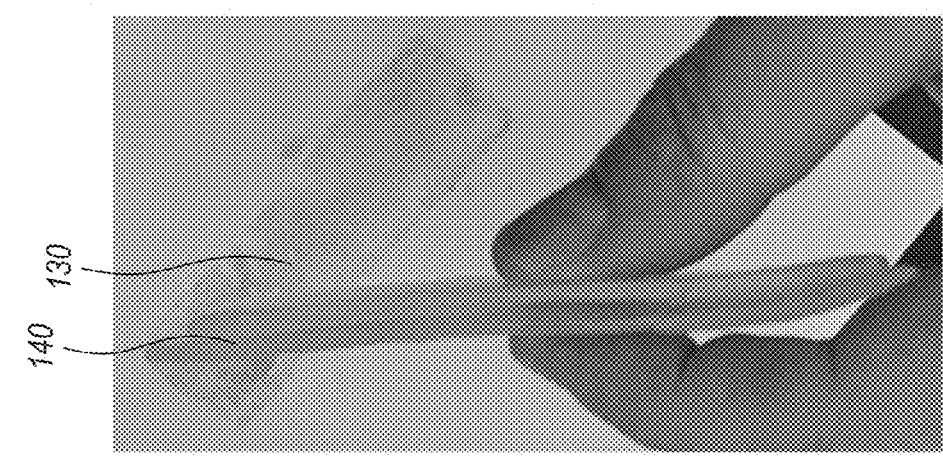
Figure 3B:
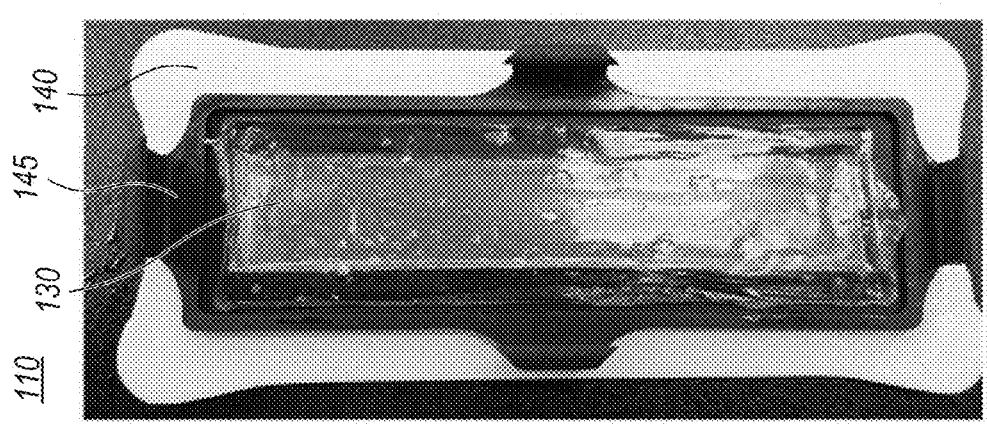
Figure 3A:
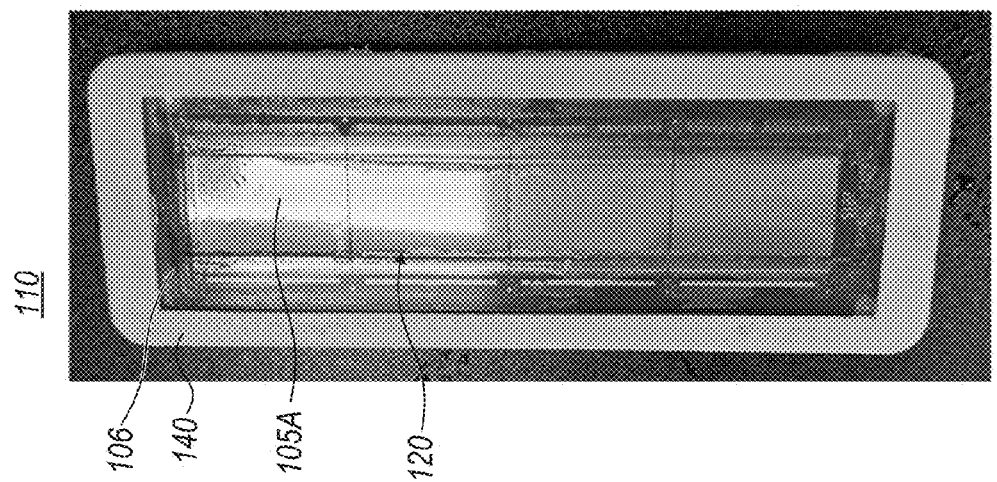
Figure 4A:
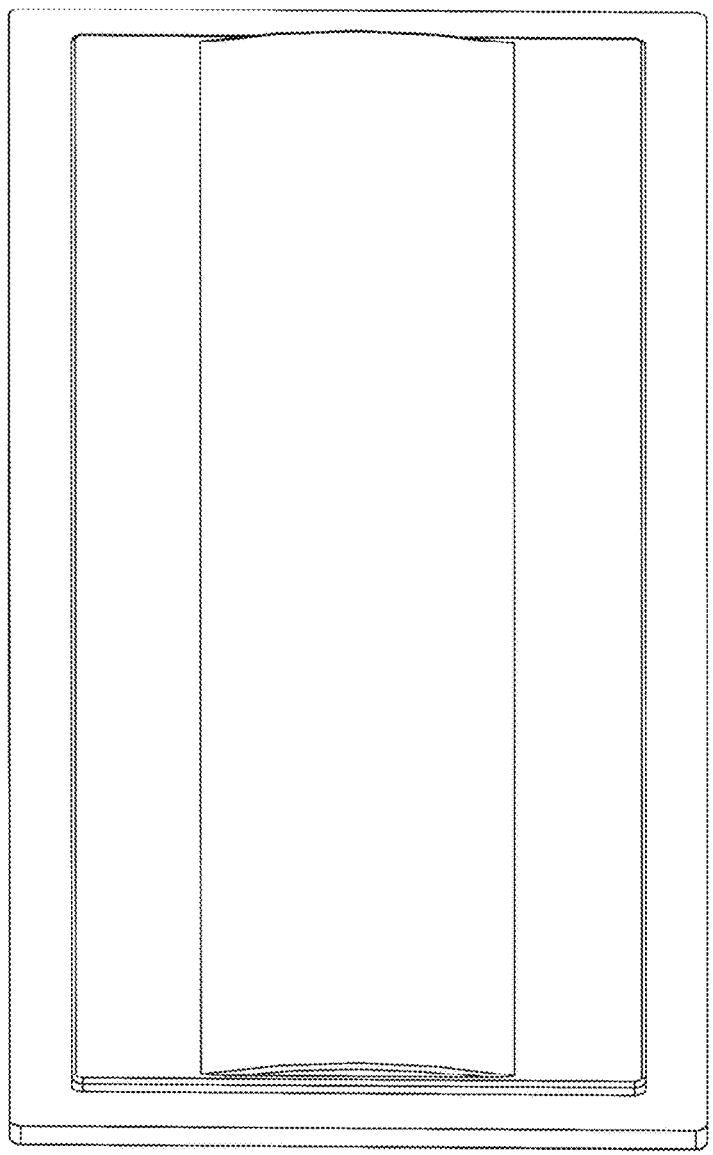
FIGS. 4A and 4B are high-level schematic top and perspective illustrations of an ultrasound lens of the low power patch, respectively, according to some embodiments of the invention.
Figure 4B:
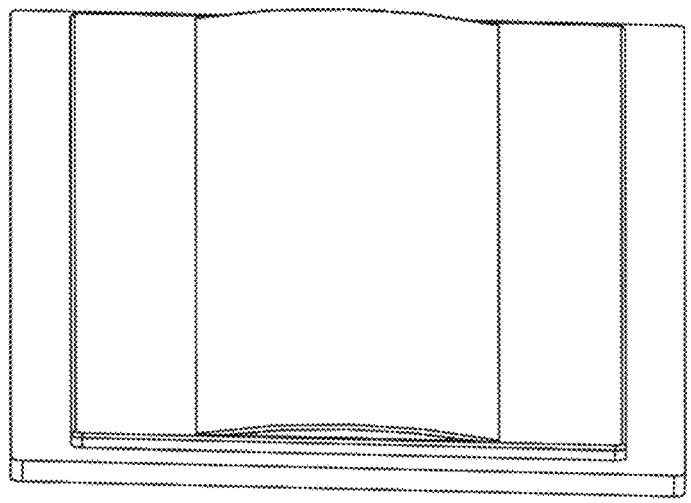

Hydrogel element 130 may be designed and implemented to provide the required ultrasound coupling between the patch and the body, possibly designed to further enhance the shape conformity between the patch and the body, and support the imaging process (see, e.g., FIGS. 3B-3D). Hydrogel element 130 may have different designs (e.g., with respect to different types of patch device 110 and/or with respect to different patients and/or body regions onto which patch device 110 is applied), which may be molded directly on patch device 110 to prevent forming air bubbles or gaps therebetween.

The UWFM ultrasound signals (104, and see, e.g., FIGS. 5, 7B, 10A and 10B) may be generated in a way that provides low power signal excitation, by generating a low amplitude coded signal that requires low voltage, low current and correspondingly very low power over the longer duty cycle (compared, e.g., to short pulses of common piezoelectric transducers)—reaching an overall heat generation that may be below 1 W. or a few mW/cm$^2$ of patch area.

The low power dissipation enables prolonged continuous operation in close contact to the human body without overheating. Moreover, disclosed systems and methods may be configured to be operate automatically and without operator interventions—to enable continuous and autonomous patient monitoring, and may be configured to provide alerts relating to specific medical conditions.

Figure 5:
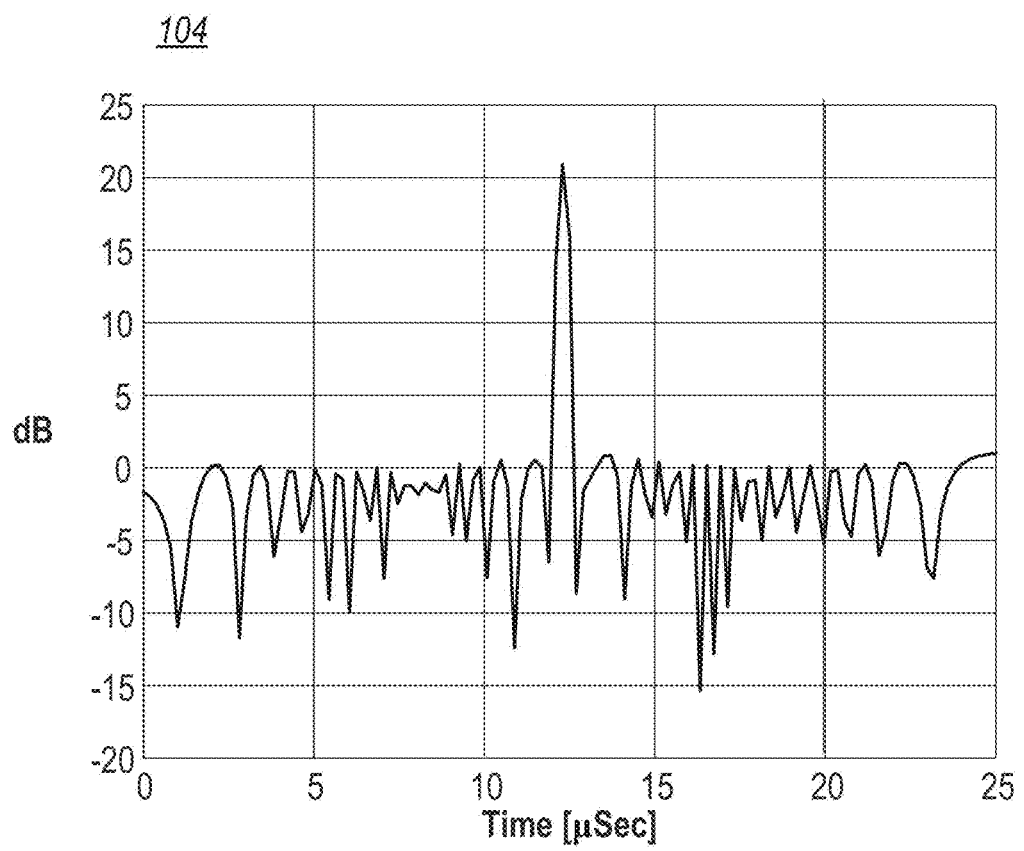
FIG. 5 provides a non-limiting example of an ultrasound signal that may be used as transmitted signal, according to some embodiments of the invention.

FIG. 5 provides a non-limiting example of an ultrasound signal that may be used as transmitted signal, according to some embodiments of the invention. FIG. 5 illustrates the axial match filter response of an NLFM pulse having a bandwidth of 3 MHz and a range resolution of 0.31 mm. Ultrawideband nonlinear frequency modulated (NLFM) may be used, in non-limiting manner, to achieve low (range) sidelobes without increasing the main-lobe width, and in certain embodiments to achieve low tolerance to the Doppler shift ensuring keeping the parameters of the NLFM pulse along the lateral direction.

In certain embodiments, the sampling rate of controller 160 may be configured to be higher than the Nyquist frequency associated with the bandwidth of the transmitted ultrasound signal (104), and a duration of the transmitted ultrasound signal and a transducer switching rate may be configured to yield an initial depth (e.g., minimal image depth illustrated schematically in FIG. 1) for the ultrasound image of at least 2 mm, 5 mm, 10 mm, intermediate or larger distances, and a Doppler frequency smaller than a few thousand Hz (e.g., 4000 Hz, 3000 Hz, 2000 Hz or intermediate values) or a few hundred Hz (e.g., 400 Hz, 300 Hz, 200 Hz or intermediate values), or intermediate values, at depths smaller than the initial depth (e.g., the minimal imaging depth denoted schematically in FIG. 1), to prevent obstruction of the ROI by bones within the initial depth from the transducers. In certain embodiments, the pulses and processing may be further configured to reduce or prevent obstructions by gas bubbles in the tissue (natural or formed by medical procedures such as ablation). In certain embodiments, the pulses and processing may be configured to reduce, minimize or prevent shadowing effects of ultrasound-opaque elements such as bones (e.g., ribs for scatterers positioned within the chest of the patient, illustrated schematically in FIG. 1 as obstructing zone 89).

In various embodiments, image processing unit 170 may comprise a match filter 172 configured to derive a tissue response by comparing the received ultrasound signal (154) to the transmitted ultrasound signal (104) from each of transducers 105A in array 105. System 100 may be configured to have a quadratic phase relationship between the transmitted ultrasound signal (104) and the received ultrasound signal (154), as illustrated in a non-limiting manner in FIGS. 6A, 6B and 7A, 7B.

Figure 6B:
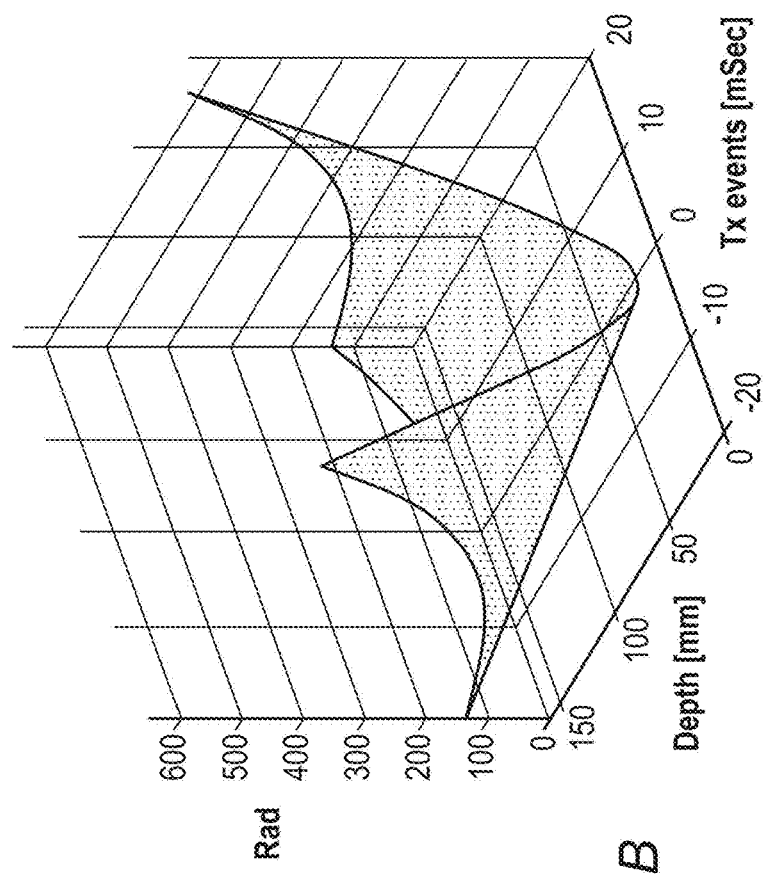
FIGS. 6A and 6B provide a non-limiting example for Range-Doppler signals for the virtual moving transducer-receiver, according to some embodiments of the invention.
Figure 6A:
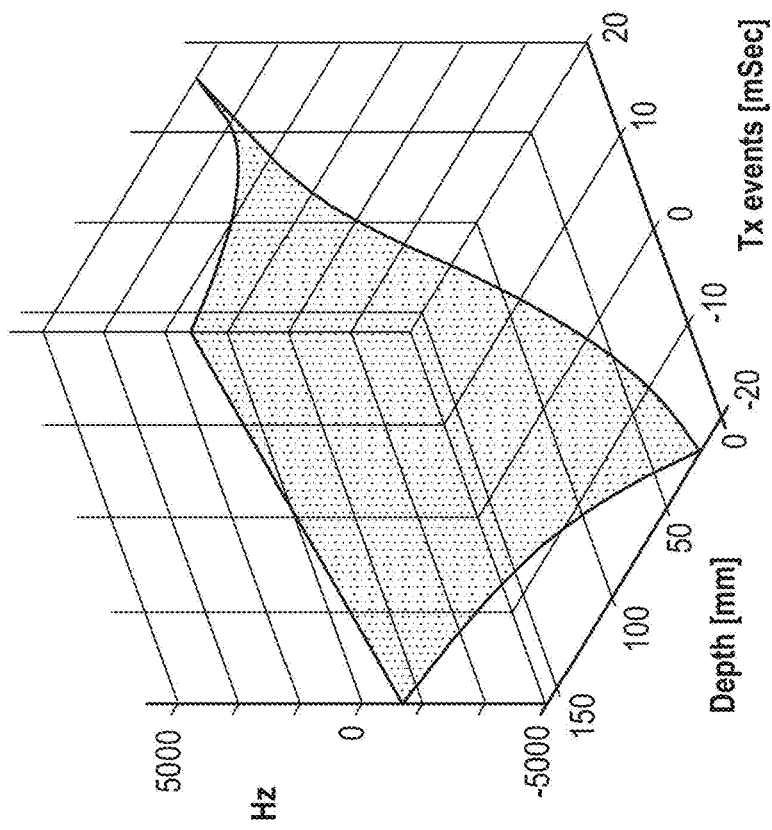

FIGS. 6A and 6B provide a non-limiting example for Range-Doppler signals for the virtual moving transducer-receiver, according to some embodiments of the invention. FIG. 6A schematically illustrates the Doppler frequency of the simulated virtually moving transducer/receiver, and FIG. 6B schematically illustrates the Doppler phase of the simulated virtually moving transducer/receiver—schematically illustrating the resulting, actual, Doppler effect. The virtual motion of the transducer along the x-axis with a velocity Vx creates the Doppler frequency (in the receiver channel) of $$F_D = \frac{2V_X}{\lambda}.$$

The scatterer located at a range r of the x-axis (e.g., on the z-axis) creates the Doppler frequency $$F_D(x, z) = \frac{2V_X}{\lambda} \sin \tan^{-1} \frac{x}{z},$$

and the phase distribution of the Doppler signal along the receiver channels is $\varphi_x(z)=2\pi F_D(x, z)\cdot T_x$, where $T_x=0$, PRI, 2PRI, ... (N−1)PRI.

Figure 7B:
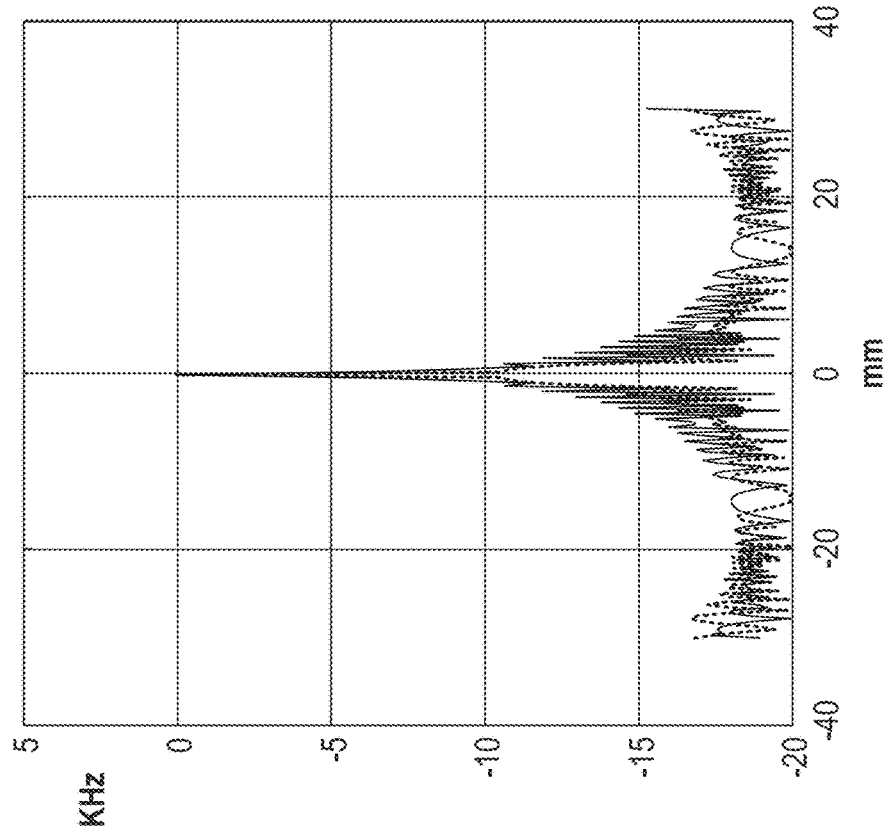
FIGS. 7A and 7B provide a non-limiting example for a lateral match filter response, according to some embodiments of the invention.
Figure 7A:
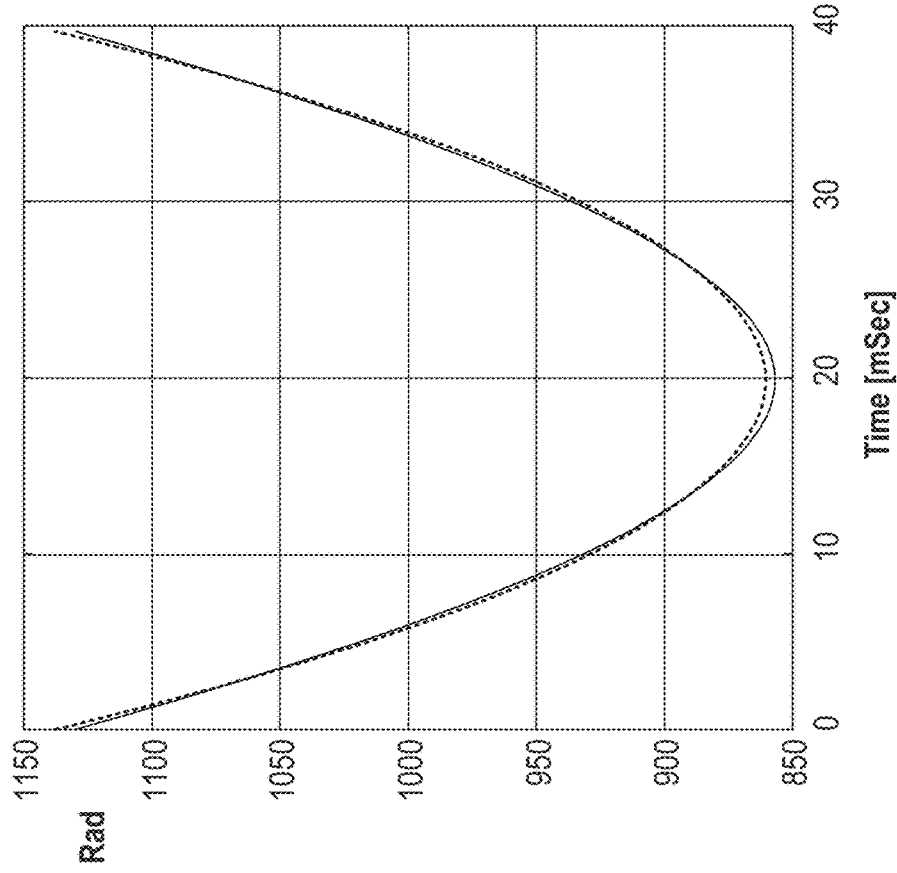

FIGS. 7A and 7B provide a non-limiting example for a lateral match filter response, according to some embodiments of the invention. FIG. 7A schematically illustrates the initial phase of the received signal from depth D=35 mm, and FIG. 7B schematically illustrates the lateral match filter response at this depth for a PRF of 4.81 kHz. The lateral resolution is dx=0.47 mm. The phase portrait of the echo received from a scatterer for the time-of-flight model is very close to the quadratic phase change (simulating a LFM—linear frequency modulated signal) along the trajectory of a moving transducer, indicating the efficient and accurate implementation of the virtual movement of the transmitter/receiver and derived results. It is noted that the quadratic phase yields a linear frequency change, e.g., from −Fd to +Fd (Fd denoting the Doppler frequency), passing through the frequencies which are close to zero. As a result, during the (lateral) reconstruction of scatterer(s) 91 at a given range, obstacles (e.g., bubbles, bones) located close to the transducer's aperture (and laid on the line of the zero frequency), e.g., in region 89 shown schematically in FIG. 1—do not interfere with the reconstruction.

Figure 8:
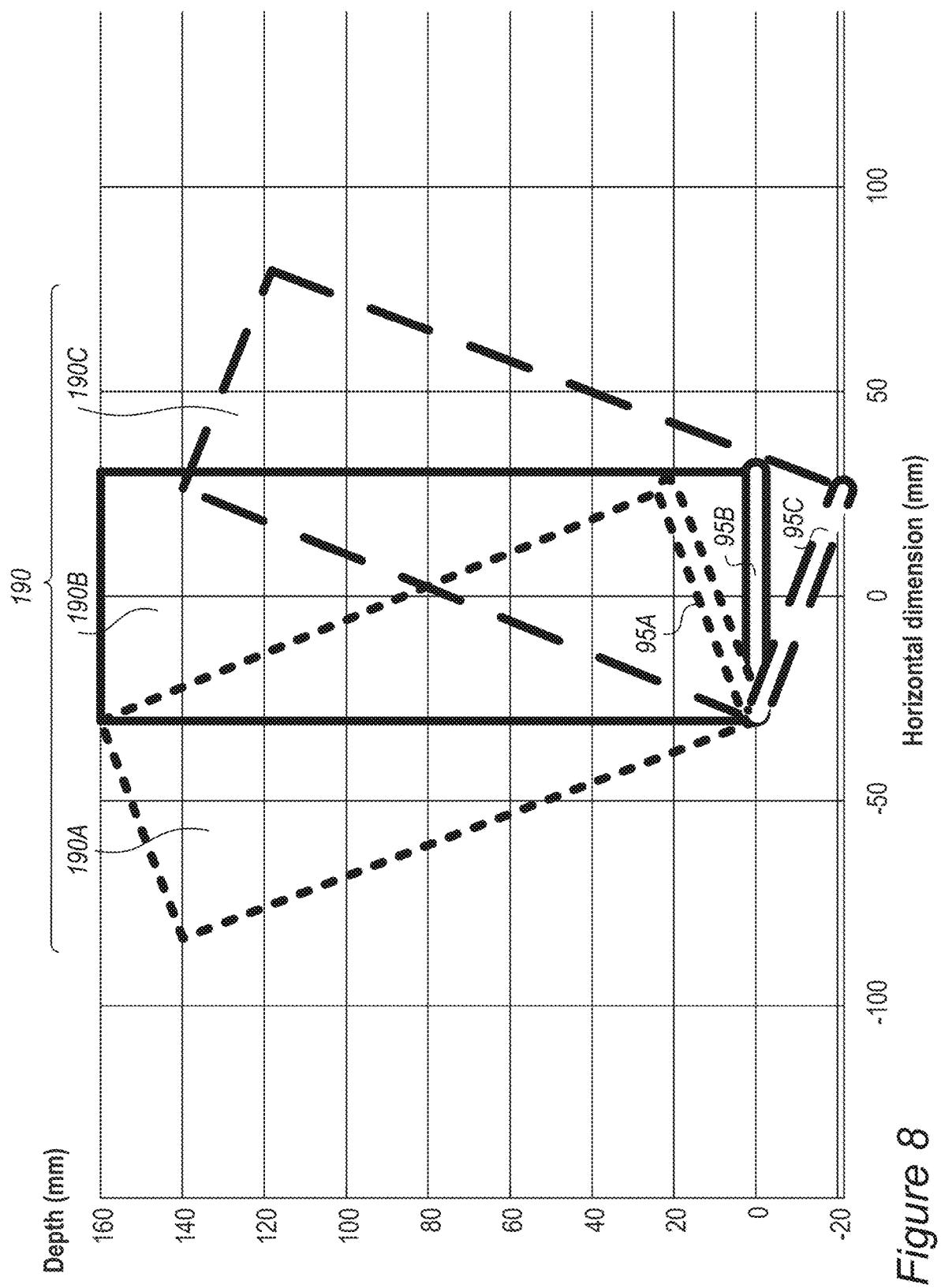
FIG. 8 is a high-level schematic illustration of the generation of a trapezoidal-like ultrasound image, according to some embodiments of the invention.

FIG. 8 is a high-level schematic illustration of the generation of a trapezoidal-like ultrasound image, according to some embodiments of the invention. In certain embodiments, image processing unit 170 may be further configured to generate a trapezoidal-like ultrasound image 190 of the ROI by combining at least three ultrasound images 190A, 190B, 190B of the ROI, each derived using different phase relations between the respective received ultrasound signals, implementing virtual steering of the virtual moving receiver to cover the corresponding area of the ROI (corresponding simulated virtual movements indicated by numerals 95A, 95B and 95C, respectively). Trapezoidal-like US image 190 may be formed from multiple rectangular windows 190A, 190B, 190B of ultrasound-reconstructed ROI by using the same (physically) array of receivers 105, but with different phases in each channel. The nonlimiting example illustrates schematically the simultaneous use of three initial phase sequences in the same receiver array to form the trapezoidal-like US image.

Figure 9:
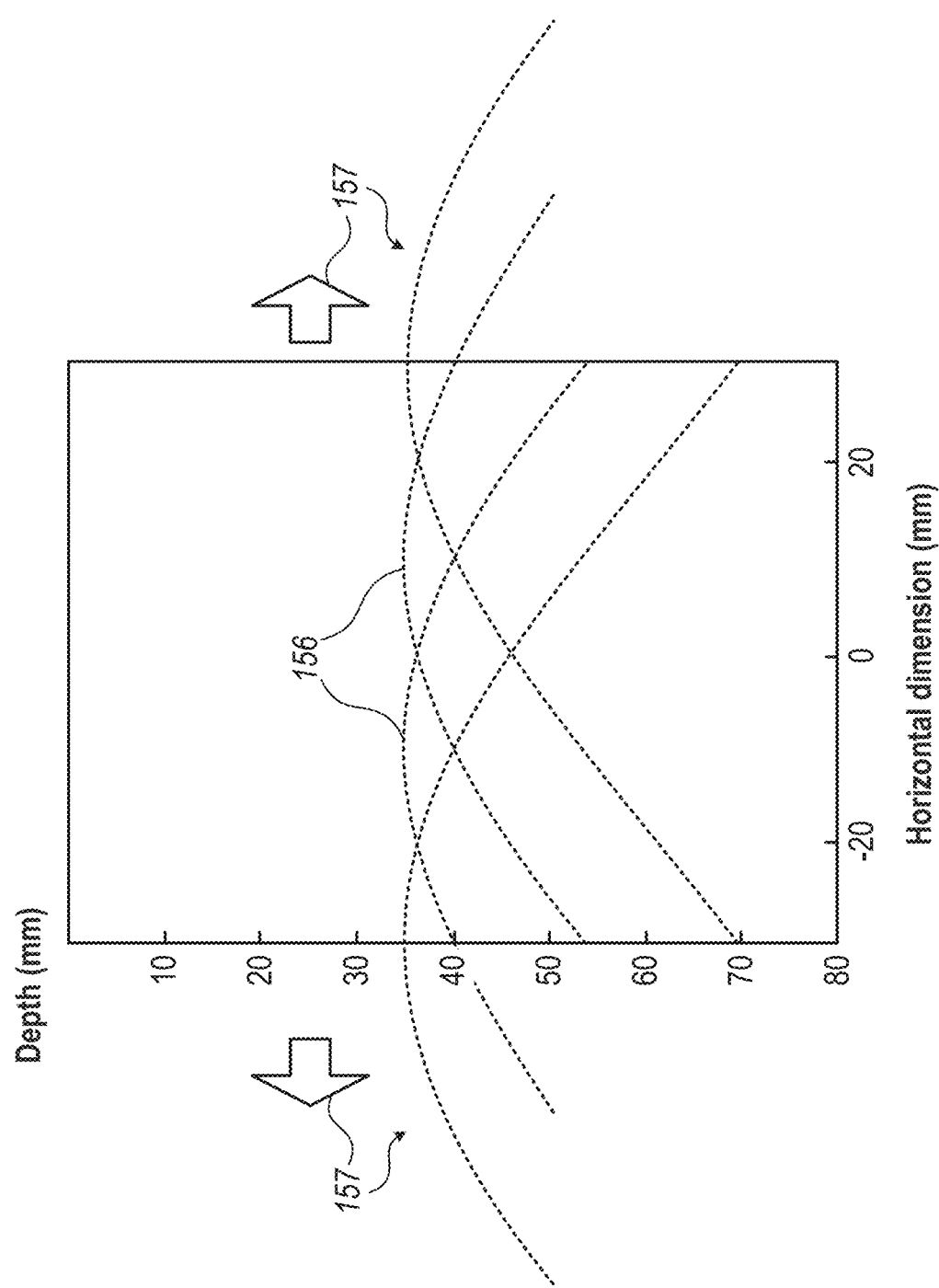
FIG. 9 is a high-level schematic illustration of the phenomenon of range migration and the disclosed extension of the peripheral range gates to augment information content and to broaden the expanse of achieved imaging, according to some embodiments of the invention.

FIG. 9 is a high-level schematic illustration of the phenomenon of range migration and the disclosed extension of the peripheral range gates to augment information content and to broaden the expanse of achieved imaging, according to some embodiments of the invention. FIG. 9 provides non-limiting data for the range migration of four simulated LFM-like signals at d=35 mm, with maximal range migration equaling 225 ranges, demonstrating the range-gate spread of the LFM-like signals coming from four different scatterers, located at the same distance from the x-axis. The finite virtual movement of the transmitter/receiver results in parabolic-like curves 156, which can be extended 157 to increase the information content of the signals and the expanse of the imaging—yielding ultrasound images 190 having larger size, higher resolution and/or higher uniformity with respect to non-augmented images. The elevation cut may be controlled by linear array 105 (e.g., focused in its near field), while the lateral cut may be created by the simulated movement of the single element (Tx/Rx) having a fan beam (in the far field)—to irradiate the ROI as wide as possible to create the range-doppler map. The lateral compression of the signals, independently for each range-gate, forms a long and narrow beam and a convolution window that is growing with the range—achieving uniformly high resolution.

Figure 10B:
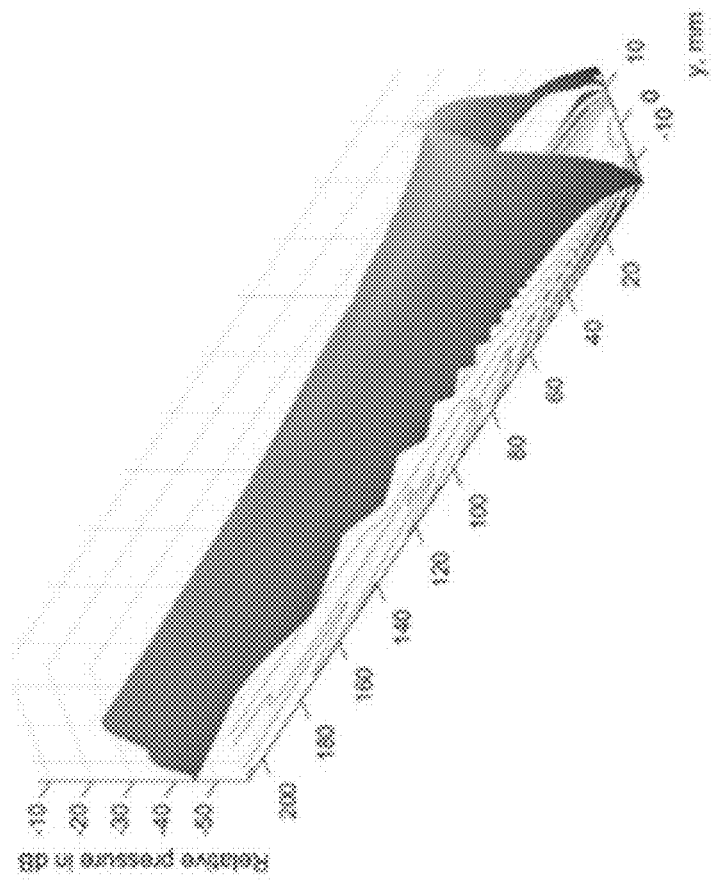
FIGS. 10A and 10B are non-limiting examples for beam configurations with an autofocusing effect, according to some embodiments of the invention.
Figure 10A:
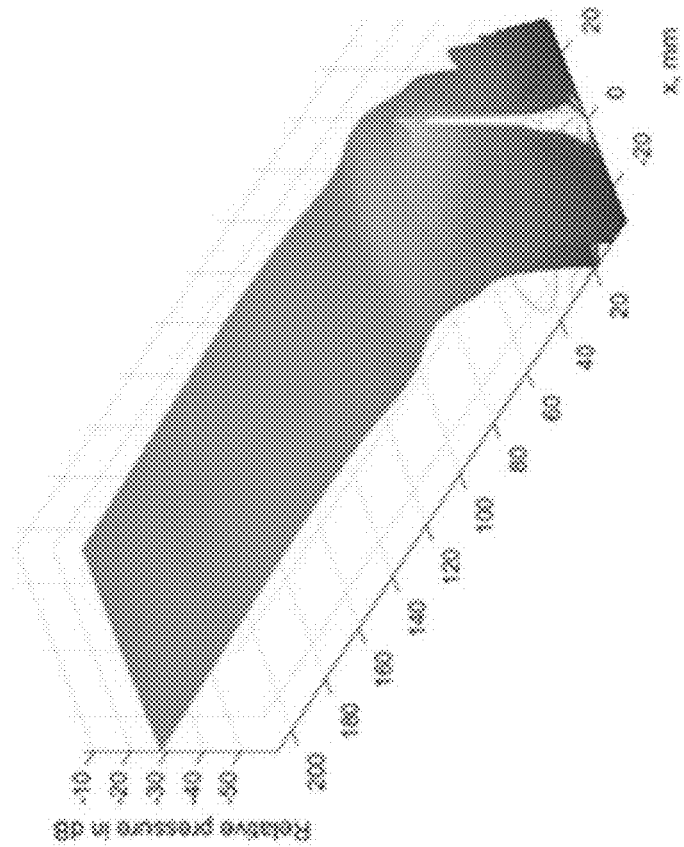

FIGS. 10A and 10B are non-limiting examples for beam configurations with an autofocusing effect, according to some embodiments of the invention. FIG. 10A illustrates a non-limited beam in the lateral x axis by single transducers 105A, while FIG. 10B illustrates a non-limited beam in the elevation y axis by array 105 of 48 transducers 105A, demonstrating an auto-focusing effect of array 105. In certain embodiments, linear array 105 of micromachined ultrasound transducers 105A may be arranged in an asymmetric pattern configured to provide the autofocusing effect. The beam may be configured to comprise a narrow elevation beam with almost constant beamwidth of about 5-30 mm, e.g., 10 mm, 15 mm or any other intermediate value, all along the imaging depth up to between 100-300 mm, e.g., 100 mm, 130 mm, 160 mm, 200 mm or any other intermediate value. The lateral cut shows a wide-angle pattern similar to the far-field pattern of the single element which results in an advantageous power reduction (in free space) proportional to $P(r) \sim 1/r^2$ (corresponding to the far field) instead of $P(r) \sim 1/r^4$ (corresponding to the near field) as would be the case for prior art designs, especially as body tissues are very dissipative to ultrasound radiation.

Figure 11:
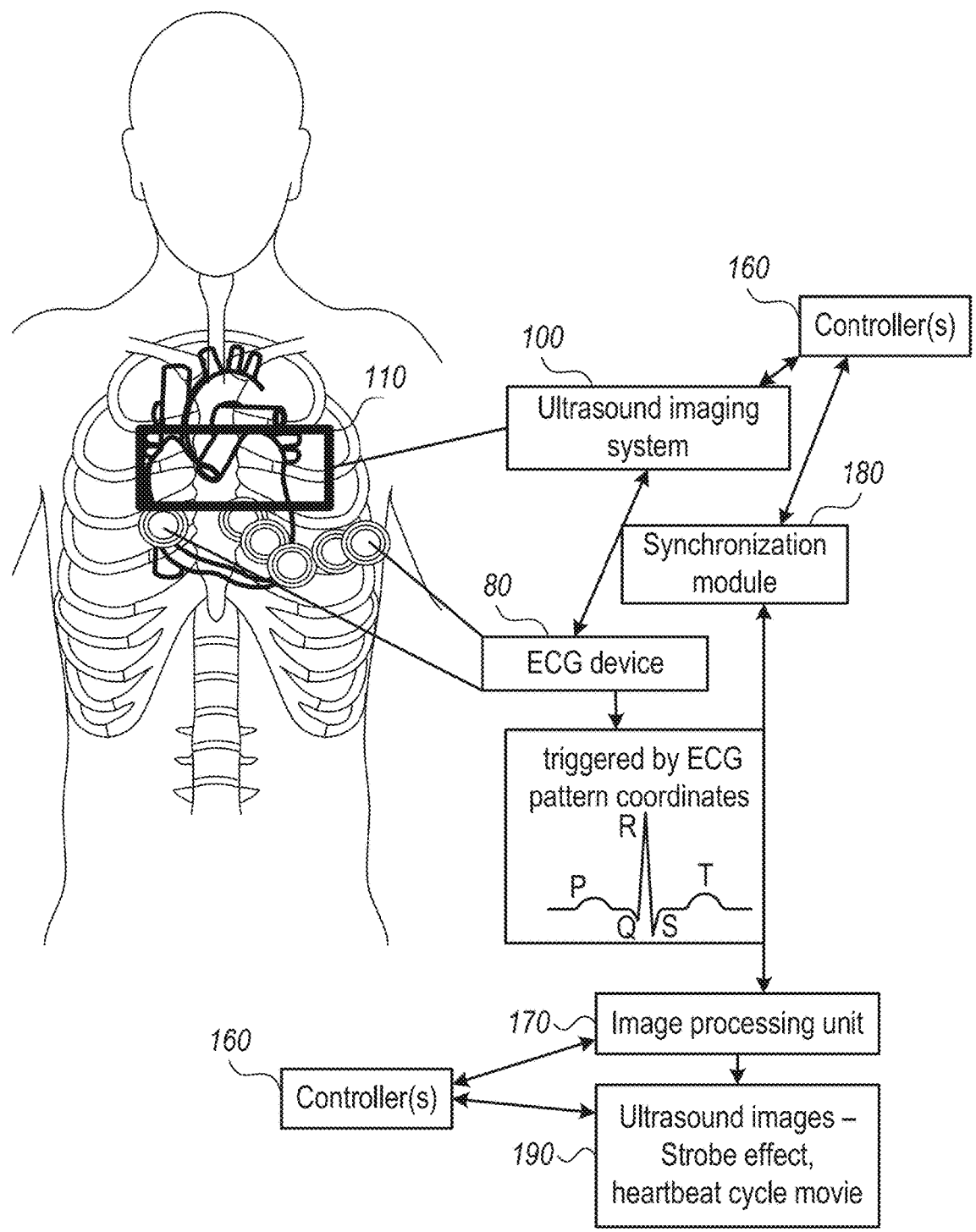
FIG. 11 is a high-level schematic block diagram of the ultrasound imaging system associated with an electrocardiogram (ECG) device, according to some embodiments of the invention.

FIG. 11 is a high-level schematic block diagram of ultrasound imaging system 100 associated with an electrocardiogram (ECG) device 80, according to some embodiments of the invention. Disclosed ultrasound imaging systems 100 may be used in conjunction with electrocardiogram (ECG) device 80, possibly in synchronization therewith, to provide integrated patient monitoring. For example, the ultrasound signals may be synchronized with respect to the ECG readings (e.g., by a synchronization module 180, being part of, or associated with ultrasound imaging system 100) to yield a strobe-effect that provides multiple instantaneous images 190 (e.g., of the heart) that correspond to specific ECG events (e.g., peaks or extrema of P, T, U waves and/or of the QRS complex of ECG). The strobe-effect may be achieved by changing the delay between ECG synchronization pulses and individual (or even a single) ultrasound image scan(s), providing images 190 of the different phases (status) of the heart beats. Image processing unit 170 (or an additional imaging unit) may be configured to accumulate the strobe-synchronized ultrasound images and generate therefrom a high resolution (spatial and/or temporal) movie of the complete heartbeat cycle (and synchronized to the ECG plot).

In contrast to prior art that needs to achieve a very high rate of ultrasound imaging in order to visualize the dynamic fast movements of structural elements of the heart (e.g., valves)—typically 100-200 frames per heart beat which is 3-4 times higher than typical US frame rate of 30-50 frames per second—disclosed strobe effect imaging 190 utilizes the synchronization between US imaging system 100 and ECG device 80 to generate multiple images of the heart at the same ECG pattern coordinates—to increase temporal and spatial resolution without the need to increase the US frame rate or even with slower rates (e.g., 10-25 frames per second, achievable by disclosed systems 100).

For example, to image the heart valves and their substructures (e.g., the edges of the valves, as non-limiting examples), the ECG signal (reflecting the electrical signals passing through the heart and the related mechanical movements of the heart and its parts) may be used to specifically identify the times in which valves open and close, and distinguish between the valves (e.g., typical valve opening durations are 40-50 msec, the closing duration for monoleaflet and bi-leaflet valves are typically <35 msec and for tri-leaflet valve typically >75 msec). As disclosed systems 100 typically sample the 20 mm sized valves in ca. 10 msec, images from multiple heartbeats may be synchronized to represent and monitor the same state of valves over multiple beats, using the ECG signal. As a result, disclosed systems 100 enable continuous monitoring at high spatial and temporal resolution, with an acceptable delay of a few minutes required to accumulate US images correlated to the ECG pattern for multiple heart cycles. In certain embodiments, machine learning and artificial intelligence algorithms may be implemented to further analyze electro-mechanical performance of the patient's heart in almost real time, e.g., at intensive care units (ICUs). The system's user interface may be configured to present the typical morphology of the heart and its parts that corresponds to any point along the ECG diagram for further consideration by a physician, and/or to create automatic alerts and indications relating to detected electro-mechanical features.

Figure 12:
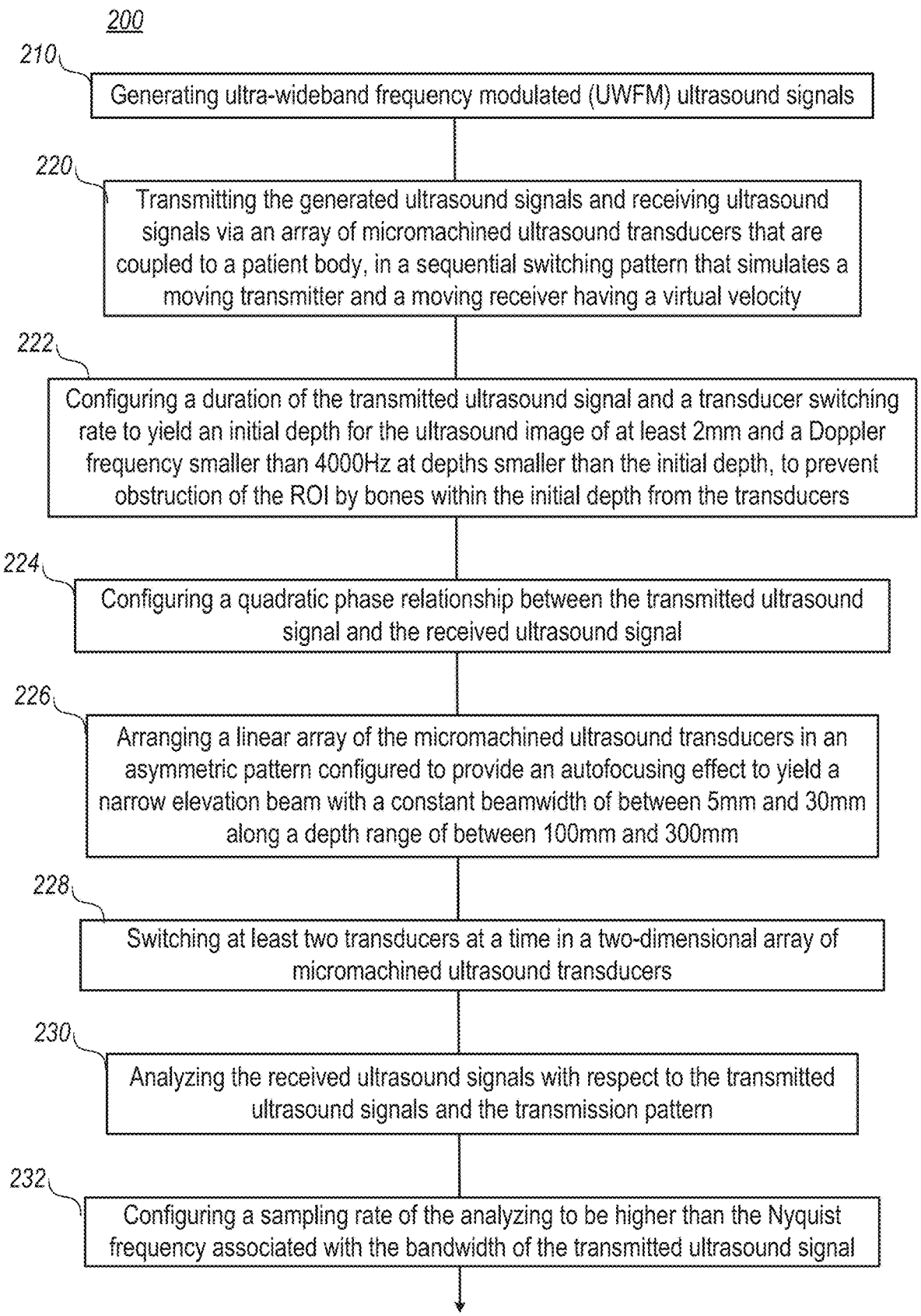
FIG. 12 is a high-level flowchart illustrating a method of ultrasound imaging, according to some embodiments of the invention.
Figure 12:
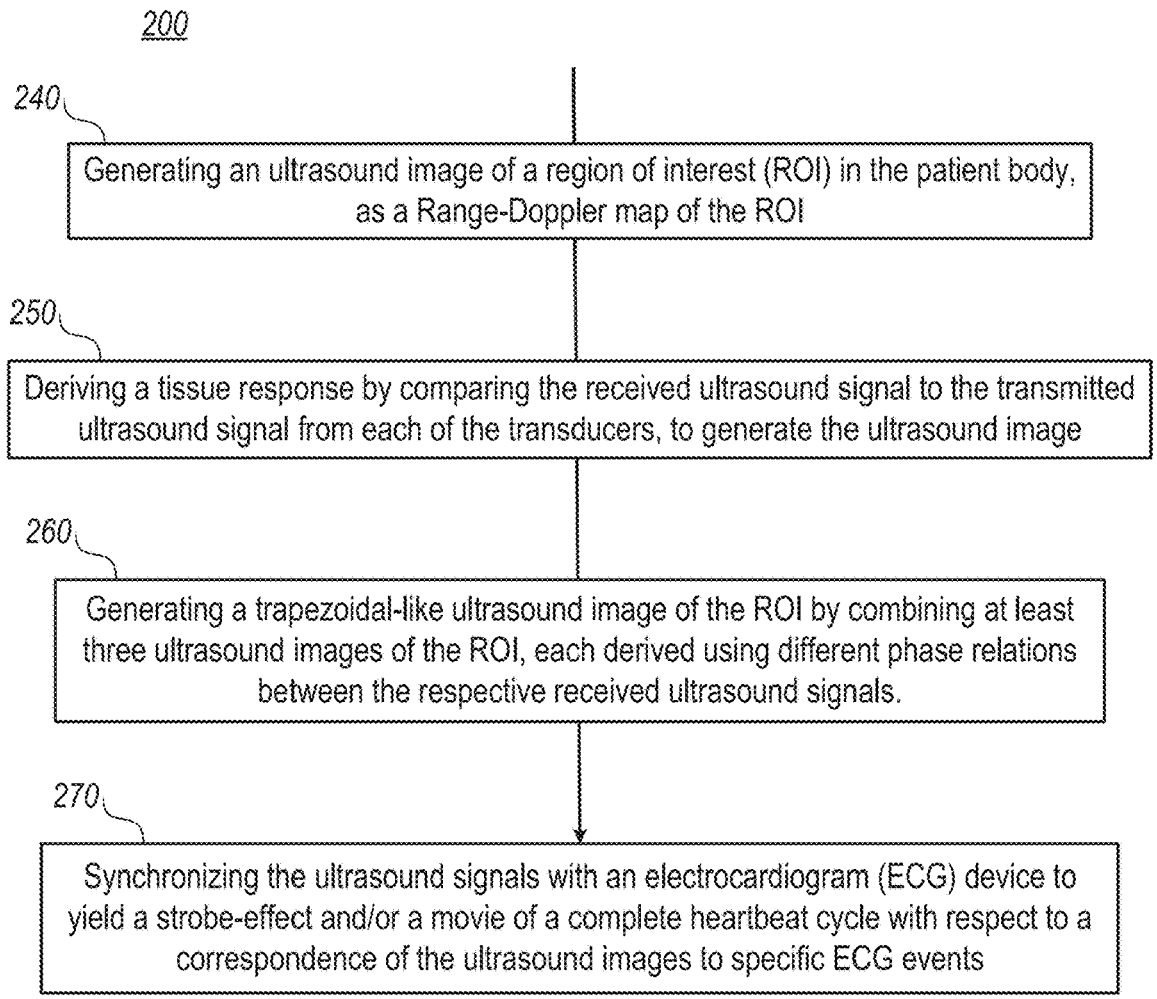

FIG. 12 is a high-level flowchart illustrating a method 200 of ultrasound imaging, according to some embodiments of the invention. The method stages may be carried out with respect to ultrasound imaging systems 100 described above, which may optionally be configured to implement method 200. Method 200 may be at least partially implemented by at least one computer processor, e.g., in controller 160, image processing unit 170. Synchronization module 180 or any other module in system 100. Certain embodiments comprise computer program products comprising a computer readable storage medium having computer readable program embodied therewith and configured to carry out the relevant stages of method 200. Method 200 may comprise the following stages, irrespective of their order.

Method 200 of ultrasound imaging may comprise generating ultra-wideband frequency modulated (UWFM) ultrasound signals (stage 210), transmitting the generated ultrasound signals and receiving ultrasound signals via an array of micromachined ultrasound transducers that are coupled to a patient body, wherein the transmitting and receiving are carried out sequentially through the transducers to the body by switching the transducers according to a predefined pattern that simulates a moving transmitter and a moving receiver having a virtual velocity (stage 220), analyzing the received ultrasound signals with respect to the transmitted ultrasound signals and the predefined transmission pattern (stage 230), and generating an ultrasound image of a region of interest (ROI) in the patient body, as a Range-Doppler map of the ROI (stage 240).

Method 200 may further comprise deriving a tissue response (e.g., as part of amazing 230 and/or generating 240) by comparing the received ultrasound signal to the transmitted ultrasound signal from each of the transducers, to generate the ultrasound image (stage 250).

Method 200 may further comprise configuring a sampling rate of the analyzing to be higher than the Nyquist frequency associated with the bandwidth of the transmitted ultrasound signal (stage 232), and configuring a duration of the transmitted ultrasound signal and a transducer switching rate to yield an initial depth for the ultrasound image of at least 2 mm and a Doppler frequency smaller than 4000 Hz at depths smaller than the initial depth, to prevent obstruction of the ROI by bones within the initial depth from the transducers (stage 222).

Method 200 may further comprise configuring a quadratic phase relationship between the transmitted ultrasound signal and the received ultrasound signal (stage 224).

Method 200 may further comprise arranging a linear array of the micromachined ultrasound transducers in an asymmetric pattern configured to provide an autofocusing effect to yield a narrow elevation beam with a constant beamwidth of between 5 mm and 30 mm along a depth range of between 100 mm and 300 mm (stage 226).

Method 200 may further comprise switching at least two transducers at a time in a two-dimensional array of micromachined ultrasound transducers (stage 228).

In certain embodiments, method 200 may further comprise generating a trapezoidal-like ultrasound image of the ROI by combining at least three ultrasound images of the ROI, each derived using different phase relations between the respective received ultrasound signals (stage 260).

In certain embodiments, method 200 may further comprise synchronizing the ultrasound signals with an electrocardiogram (ECG) device to yield a strobe-effect and/or a movie of a complete heartbeat cycle with respect to a correspondence of the ultrasound images to specific ECG events (stage 270).

Certain embodiments comprise a computer program product comprising a non-transitory computer readable storage medium having computer readable program embodied therewith, the computer readable program comprising: (i) computer readable program configured to generate ultra-wideband frequency modulated (UWFM) ultrasound signals. (ii) computer readable program configured to transmit the generated ultrasound signals and receiving ultrasound signals via an array of micromachined ultrasound transducers that are coupled to a patient body, wherein the transmitting and receiving are carried out sequentially through the transducers to the body by switching the transducers according to a predefined pattern that simulates a moving transmitter and a moving receiver having a virtual velocity, (iii) computer readable program configured to analyze the received ultrasound signals with respect to the transmitted ultrasound signals and the predefined transmission pattern, and (iv) computer readable program configured to generate an ultrasound image of a region of interest (ROI) in the patient body, as a Range-Doppler map of the ROI; and optionally computer readable program configured to implement any of the stages of method 200 or at least part(s) thereof.

Figure 13:
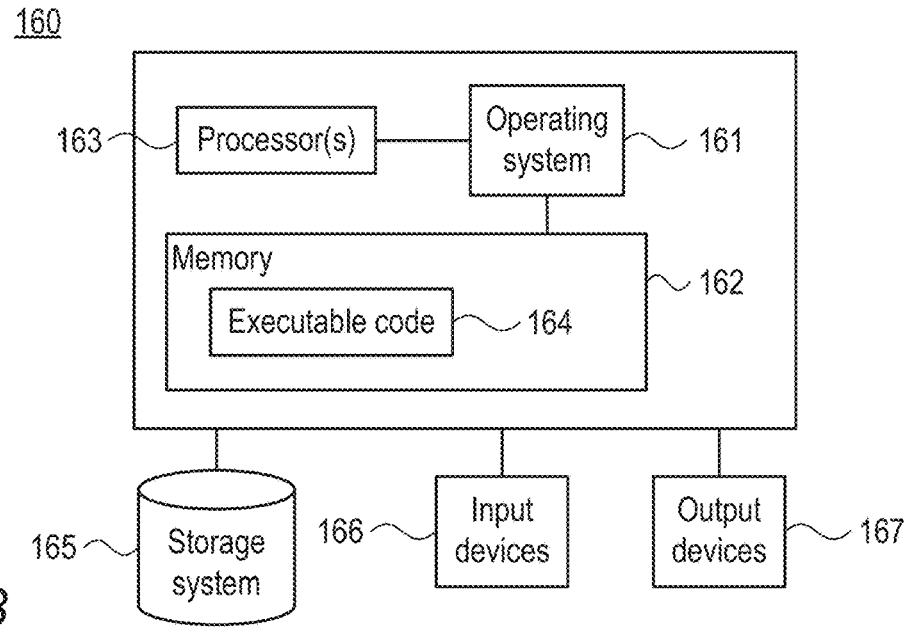
FIG. 13 is a high-level block diagram of exemplary computing device for implementing the controller(s), which may be used with embodiments of the present invention.

FIG. 13 is a high-level block diagram of exemplary computing device for implementing controller 160, which may be used with embodiments of the present invention. Controller 160 may include a processor 163 that may be or include, for example, one or more central processing unit processor(s) (CPU), one or more Graphics Processing Unit(s) (GPU or general-purpose GPU—GPGPU), a chip or any suitable computing or computational device, an operating system 161, a memory 162, a storage system 165, input devices 166 and output devices 167. The processors may comprise multiple cores configured to enable parallel processing of different tasks, for example processing of different stages and/or parts of method 200.

Operating system 161 may be or may include any code segment designed and/or configured to perform tasks involving coordination, scheduling, arbitration, supervising, controlling, or otherwise managing operation of controller 160, for example, scheduling execution of programs. Memory 162 may be or may include, for example, a Random-Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short-term memory unit, a long-term memory unit, or other suitable memory units or storage units. Memory 162 may be or may include a plurality of possibly different memory units. Memory 162 may store for example, instructions to carry out a method (e.g., code 164), and/or data such as user responses, interruptions, etc.

Executable code 164 may be any executable code, e.g., an application, a program, a process, task or script. Executable code 164 may be executed by processor 163 possibly under control of operating system 161. For example, executable code 164 may when executed cause the production or compilation of computer code, or application execution such as VR execution or inference, according to embodiments of the present invention. Executable code 164 may be code produced by methods described herein. For the various modules and functions described herein, one or more controllers 160 or components of controller 160 may be used. Devices that include components similar or different to those included controller 160 may be used and may be connected to a network and used as a system. One or more processor(s)

163 may be configured to carry out embodiments of the present invention by for example executing software or code.

Storage system 165 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, VR model data, parameters, etc. may be stored in a storage system 165 and may be loaded from storage system 165 into a memory 162 where it may be processed by processor 163. In some embodiments, some of the components shown in FIG. 13 may be omitted.

Input devices 166 may be or may include for example a mouse, a keyboard, a touch screen or pad or any suitable input device. It will be recognized that any suitable number of input devices may be operatively connected to controller 160 as shown by block 166. Output devices 167 may include one or more displays, speakers and/or any other suitable output devices. It will be recognized that any suitable number of output devices may be operatively connected to controller 160 as shown by block 167. Any applicable input/output (I/O) devices may be connected to controller 160, for example, a wired or wireless network interface card (NIC), a modem, printer or facsimile machine, a universal serial bus (USB) device or external hard drive may be included in input devices 166 and/or output devices 167.

Embodiments of the invention may include one or more article(s) (e.g., memory 162 or storage system 165) such as a computer or processor non-transitory readable medium, or a computer or processor non-transitory storage medium, such as for example a memory, a disk drive, or a USB flash memory, encoding, including or storing instructions. e.g., computer-executable instructions, which, when executed by a processor or controller, carry out methods disclosed herein.

Figure 14:
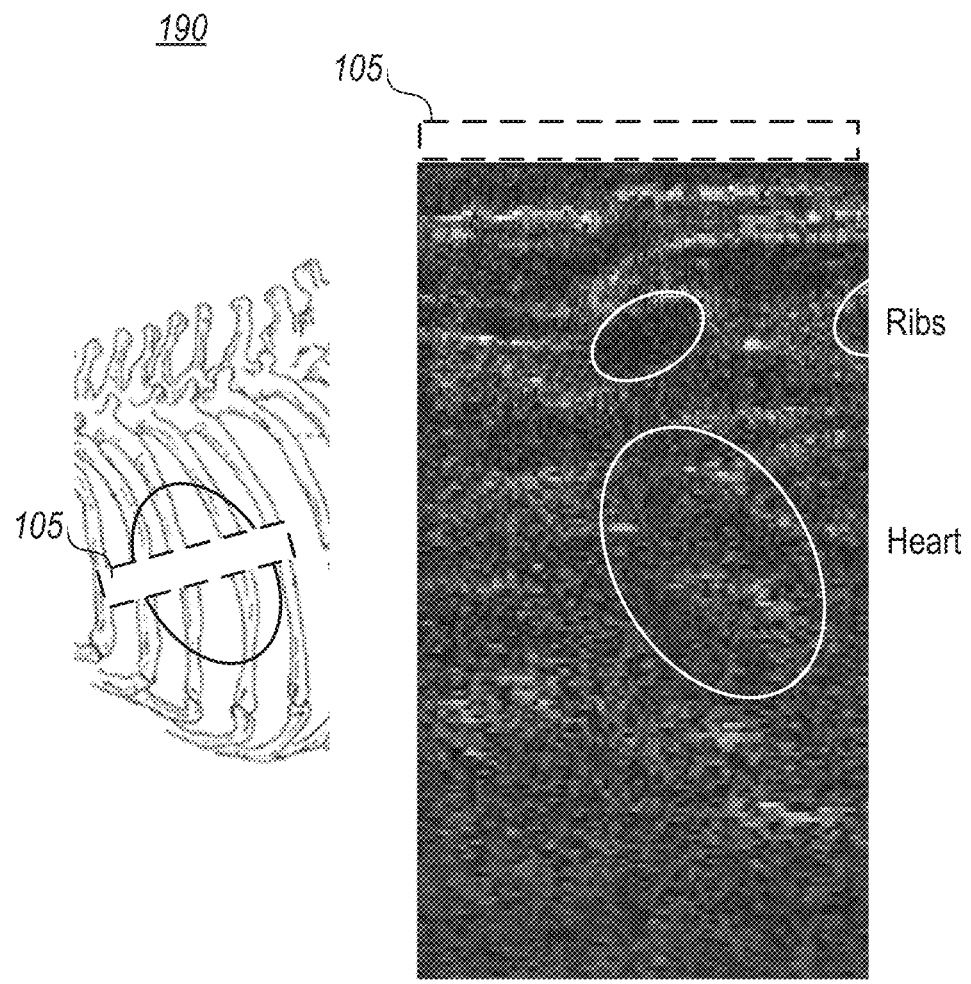
FIG. 14 is an annotated ultrasound image showing the ultrasound imaging of the heart through the rib cage, using systems disclosed in embodiments of the present invention.

FIG. 14 is an annotated ultrasound image 190 showing the ultrasound imaging of the heart through the rib cage, using system 100 disclosed in embodiments of the present invention. The schematic image indicates the approximate anatomical structures, and the annotations on ultrasound image 190 indicated the imaging of the heart through the ribs, which in prior art systems obstruct and do not allow ultrasound imaging of the heart.

Elements from FIGS. 1-14 may be combined in any operable combination, and the illustration of certain elements in certain figures and not in others merely serves an explanatory purpose and is non-limiting. It is noted that disclosed values may be modified by ±10%.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram or portions thereof.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment". "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments.

Other possible variations, modifications, and applications are also within the scope of the invention. Accordingly, the scope of the invention should not be limited by what has thus far been described, but by the appended claims and their legal equivalents.

What is claimed is:

1. An ultrasound imaging system comprising:
a source configured to generate an ultra-wideband frequency modulated (UWFM) ultrasound signal that has a time-bandwidth product (TBP) that is larger than 1,
at least one linear array of micromachined ultrasound transducers, configured to be coupled to a patient body,
a controller configured to transmit the generated ultrasound signal and to receive an ultrasound signal from the patient body—sequentially through the transducers to the body by switching the transducers according to a predefined pattern, and
an image processing unit configured to analyze the received ultrasound signals with respect to the transmitted ultrasound signals and the predefined transmission pattern and generate a far-field ultrasound image of a region of interest (ROI) in the patient body,
wherein:
the predefined pattern includes switching one transducer at a time and simulates a moving transmitter and a moving receiver having a virtual velocity which yields a Doppler effect,
the image processing unit comprises a match filter configured to derive a tissue response by comparing the received ultrasound signal to the transmitted ultrasound signal from each of the transducers, and
the image processing unit is configured to generate, from the derived tissue response, the ultrasound image as a Range-Doppler map of the ROI.

2. The ultrasound imaging system of claim 1, wherein:
a sampling rate of the controller is configured to be higher than the Nyquist frequency associated with the bandwidth of the transmitted ultrasound signal, and
a duration of the transmitted ultrasound signal and a transducer switching rate are configured to yield an initial depth for the ultrasound image of at least 2 mm and a Doppler frequency smaller than 4000 Hz at depths smaller than the initial depth, to prevent obstruction of the ROI by bones within the initial depth from the transducers.

3. The ultrasound imaging system of claim 1, wherein the at least one linear array of micromachined ultrasound transducers is configured to generate transduction in an asymmetric pattern with respect to a lateral direction and an elevation direction, configured to provide a fan-beam in the lateral direction and a narrow beam in the elevation direction, with an autofocusing effect providing the narrow elevation beam having a constant beamwidth of between 5 mm and 30 mm along a depth range of between 100 mm and 300 mm.

4. The ultrasound imaging system of claim 1, wherein the at least one linear array of micromachined ultrasound transducers comprises two linear arrays of transducers to yield a two-dimensional array of transducers, and the predefined pattern includes switching at least two transducers one transducer from each linear array at any one time.

5. The ultrasound imaging system of claim 1, wherein the micromachined ultrasound transducers comprise capacitive micromachined ultrasound transducers (CMUTs) and/or piezoelectric micromachined ultrasonic transducers (PMUTs).

6. The ultrasound imaging system of claim 1, wherein the image processing unit is further configured to generate an ultrasound image of the ROI by combining at least three ultrasound images of the ROI, each derived using different phase relations between the respective received ultrasound signals.

7. The ultrasound imaging system of claim 1, further comprising a synchronization module configured to synchronize the ultrasound signals with an electrocardiogram (ECG) device to yield a strobe-effect and/or a movie of a complete heartbeat cycle with respect to a correspondence of the ultrasound images to specific ECG events.

8. A method of ultrasound imaging, the method comprising:
generating ultra-wideband frequency modulated (UWFM) ultrasound signals that have a time-bandwidth product (TBP) that is larger than 1,
transmitting the generated ultrasound signals and receiving ultrasound signals via at least one linear array of micromachined ultrasound transducers that are coupled to a patient body, wherein the transmitting and receiving are carried out sequentially through the transducers to the body by switching the transducers one at a time according to a predefined pattern that simulates a moving transmitter and a moving receiver having a virtual velocity which yields a Doppler effect,
analyzing the received ultrasound signals with respect to the transmitted ultrasound signals and the predefined transmission pattern,
deriving a tissue response by comparing the received ultrasound signal to the transmitted ultrasound signal from each of the transducers, and
generating, from the derived tissue response, a far-field ultrasound image of a region of interest (ROI) in the patient body, as a Range-Doppler map of the ROI.

9. The method of claim 8, further comprising:
configuring a sampling rate of the analyzing to be higher than the Nyquist frequency associated with the bandwidth of the transmitted ultrasound signal, and
configuring a duration of the transmitted ultrasound signal and a transducer switching rate to yield an initial depth for the ultrasound image of at least 2 mm and a Doppler frequency smaller than 4000 Hz at depths smaller than the initial depth, to prevent obstruction of the ROI by bones within the initial depth from the transducers.

10. The method of claim 8, further comprising arranging the at least one linear array of the micromachined ultrasound transducers to generate transduction in an asymmetric pattern with respect to a lateral direction and an elevation direction, to provide a fan-beam in the lateral direction and a narrow beam in the elevation direction, with an autofocusing effect providing the narrow elevation beam having a constant beamwidth of between 5 mm and 30 mm along a depth range of between 100 mm and 300 mm.

11. The method of claim 8, wherein the at least one linear array of micromachined ultrasound transducers comprises two linear arrays of transducers to yield a two-dimensional array of transducers, and the method further comprises switching at least two transducers, one transducer from each linear array at any one time in the two-dimensional array of micromachined ultrasound transducers.

12. The method of claim 8, further comprising generating an ultrasound image of the ROI by combining at least three ultrasound images of the ROI, each derived using different phase relations between the respective received ultrasound signals.

13. The method of claim 8, further comprising synchronizing the ultrasound signals with an electrocardiogram (ECG) device to yield a strobe-effect and/or a movie of a complete heartbeat cycle with respect to a correspondence of the ultrasound images to specific ECG events.

14. A computer program product comprising a non-transitory computer readable storage medium having computer readable program embodied therewith, the computer readable program comprising:

computer readable program configured to generate ultra-wideband frequency modulated (UWFM) ultrasound signals that have a time-bandwidth product (TBP) that is larger than 1, computer readable program configured to transmit the generated ultrasound signals and receiving ultrasound signals via a linear array of micromachined ultrasound transducers that are coupled to a patient body, wherein the transmitting and receiving are carried out sequentially through the transducers to the body by switching the transducers one at a time according to a predefined pattern that simulates a moving transmitter and a moving receiver having a virtual velocity which yields a Doppler effect, computer readable program configured to analyze the received ultrasound signals with respect to the transmitted ultrasound signals and the predefined transmission pattern, computer readable program configured to derive a tissue response by comparing the received ultrasound signal to the transmitted ultrasound signal from each of the transducers, and computer readable program configured to generate, from the derived tissue response, a far-field ultrasound image of a region of interest (ROI) in the patient body, as a Range-Doppler map of the ROI.

* * * * *